US006998402B2

(12) United States Patent
Niewöhner et al.

(10) Patent No.: US 6,998,402 B2
(45) Date of Patent: Feb. 14, 2006

(54) SUBSTITUTED IMIDAZOTRIAZINONES

(75) Inventors: Ulrich Niewöhner, deceased, late of Wermelskirchen (DE); by Maria Theresia Niewöhner, legal representative, Wermelskirchen (DE); Dagmar Schauss, Solingen (DE); Gerhard König, Arlington, MA (US); Martin Hendrix, Odenthal (DE); Frank-Gerhard Böss, Wuppertal (DE); Franz-Josef van der Staay, Lohmar (DE); Rudy Schreiber, Menlo Park, CA (US); Karl-Heinz Schlemmer, Wuppertal (DE); Toshiya Moriwaki, Nara-ken (JP)

(73) Assignee: Bayer Aktiengesellschaft, Leverkusen (DE)

( * ) Notice: Subject to any disclaimer, the term of this patent is extended or adjusted under 35 U.S.C. 154(b) by 27 days.

(21) Appl. No.: 10/468,511

(22) PCT Filed: Feb. 11, 2002

(86) PCT No.: PCT/EP02/01392

§ 371 (c)(1),
(2), (4) Date: Feb. 23, 2004

(87) PCT Pub. No.: WO02/068423

PCT Pub. Date: Sep. 6, 2002

(65) Prior Publication Data

US 2005/0009822 A1    Jan. 13, 2005

(30) Foreign Application Priority Data

Feb. 23, 2001   (DE) ................................ 101 08 752

(51) Int. Cl.
*C07D 487/04*   (2006.01)
*C07D 253/06*   (2006.01)
*A61K 31/53*   (2006.01)
*A61P 25/00*   (2006.01)

(52) U.S. Cl. ...................................... 514/243; 544/184
(58) Field of Classification Search ................ 544/184; 514/243

See application file for complete search history.

(56) References Cited

U.S. PATENT DOCUMENTS 6,362,178 B1    3/2002   Niewohner et al. ......... 514/218

FOREIGN PATENT DOCUMENTS

WO          9924433         5/1999

OTHER PUBLICATIONS

Lucas et al. Pharmacological Reviews 52 (3), 375-413, 2000.*
Bonkale et al. Neuroscience Letters 187:5-8, 1995.*
de Vente Neurochem. Int. 45(6):799-812, 2004.*
West, Anthony R., Solid State Chemistry and Its Applications, Wiley, New York, 1988, pp. 358 & 365.*

* cited by examiner

*Primary Examiner*—Venkataraman Balasubramanian
(74) *Attorney, Agent, or Firm*—Susan M. Pellegrino

(57) ABSTRACT

The invention relates to novel substituted imidazotriazinones, to a method for their production and to the use thereof for producing medicaments, in particular to improve perception, powers of concentration, learning capacity and/or memory retentiveness.

11 Claims, No Drawings

SUBSTITUTED IMIDAZOTRIAZINONES

The present invention relates to new substituted imidazotriazinones, processes for their preparation, and their use for the production of medicaments, in particular for improving perception, concentration power, learning power and/or memory power.

Phosphodiesterases (PDEs) play an essential role in the regulation of the intracellular cGMP and cAMP levels. Of the previously described phosphodiesterase isoenzyme groups PDE 1 to PDE 10 (Beavo and Reifsnyder *Trends in Pharmacol. Sci.* 1990, 11, 150–155; Sonderling and Beavo *Curr. Opin. Cell Biol.* 2000, 12, 174–179), the PDEs 1, 2, 5, 9 and 10 are mainly responsible for the metabolism of cGMP. On account of the varying distribution of these cGMP-metabolizing PDEs in the tissue, selective inhibitors should raise the cGMP levels in the corresponding tissue, depending on the tissue distribution of the appropriate isoenzyme.

The particular feature of PDE 2 lies in its positive cooperative kinetics with respect to the substrate cGMP. It was postulated that small amounts of cGMP bind to the so-called cGMP-binding domain and thereby bring about activation of the enzyme. By this means, the affinity of the catalytic domain to cGMP and cAMP is also increased (Martins et al. *J. Biol. Chem.* 1982, 257, 1973–1979). Therefore PDE 2 can hydrolyse and thereby also control both second messenger systems by means of small amounts of cGMP.

PDE 2 has been isolated from various tissues, for example from heart, adrenal gland, liver, platelets and in particular brain. In the brain, PDE 2 mRNA is expressed strongly in the cortex, the basal ganglia and in the hippocampus (Sonnenburg et al. *Biol. Chem.* 1991, 266, 17655–17661). The sequence of the human isoform PDE 2A3 was reported by Rosman et al. *Gene* 1997, 191, 89–95. Of the tissues investigated, the expression of PDE 2A was demonstrated strongly therein in the brain and heart and more weakly in liver, skeletal muscle, kidney and pancreas.

U.S. Pat. No. 4,278,673 discloses imidazopyrimidinones having cAMP PDE-inhibitory action for the treatment of asthma and bronchitis.

WO-A-99/67244 and WO-A-99/24433 disclose 7-alkyl-2-phenyl-imidazotriazinones having PDE 5-inhibiting action for the treatment of vascular diseases.

EP-A-0 771 799, WO-A-98/40384 and WO-A-00/12504 describe purinone, allopurinol and triazolopyrimidinone derivatives, their inhibitory action on cGMP-metabolizing PDEs and their suitability for the treatment of vascular diseases.

The present invention relates to compounds of the general formula (I),

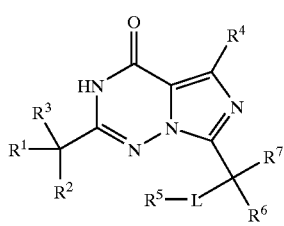

(I)

in which
$R^1$ denotes phenyl which can be substituted up to three times identically or differently by radicals selected from the group consisting of $(C_1–C_4)$-alkyl, $(C_1–C_4)$-alkoxy, halogen, cyano, —$NHCOR^8$, —$NHSO_2R^9$, —$SO_2NR^{10}R^{11}$, —$SO_2R^{12}$, and —$NR^{13}R^{14}$,
in which
$R^8$, $R^{10}$, $R^{11}$, $R^{13}$ and $R^{14}$ independently of one another are hydrogen or $(C_1–C_4)$-alkyl, and
$R^9$ and $R^{12}$ independently of one another are $(C_1–C_4)$-alkyl,
or
$R^{10}$ and $R^{11}$ together with the adjacent nitrogen atom form an azetidin-1-yl, pyrrol-1-yl, piperid-1-yl, azepin-1-yl, 4-methyl-piperazin-1-yl or morpholin-1-yl radical,
or
$R^{13}$ and $R^{14}$ together with the adjacent nitrogen atom form an azetidin-1-yl, pyrrol-1-yl, piperid-1-yl, azepin-1-yl, 4-methyl-piperazin-1-yl or morpholin-1-yl radical,
$R^2$ and $R^3$ independently of one another denote hydrogen or fluorine,
$R^4$ denotes $(C_1–C_4)$-alkyl,
$R^5$ denotes $(C_1–C_3)$-alkyl,
$R^6$ denotes hydrogen or methyl,
$R^7$ denotes $(C_1–C_{10})$-alkyl, $(C_2–C_{10})$-alkenyl or $(C_2–C_{10})$-alkinyl, and
L denotes carbonyl or hydroxymethanediyl,
and their physiologically tolerable salts, hydrates and/or solvates.

$(C_1–C_{10})$-Alkyl, $(C_1–C_4)$-alkyl, $(C_1–C_3)$-alkyl and $(C_4–C_7)$-alkyl in the context of the invention represent a straight-chain or branched alkyl radical having 1 to 10, 1 to 4, 1 to 3 and 4 to 7 carbon atoms, respectively. Examples which may be mentioned are: methyl, ethyl, n-propyl, isopropyl, n-butyl, t-butyl, n-pentyl, n-hexyl and n-heptyl.

$(C_2–C_{10})$-Alkenyl and $(C_4–C_7)$-alkenyl in the context of the invention represent a straight-chain or branched alkenyl radical having 2 to 10 carbon atoms and 4 to 7 carbon atoms, respectively. Examples which may be mentioned are: vinyl, allyl, isopropenyl, n-but-2-en-1-yl, n-pent-4-en-1-yl and n-hex-5-en-1-yl.

$(C_2–C_{10})$-Alkinyl in the context of the invention represents a straight-chain or branched alkinyl radical having 2 to 10 carbon atoms. Examples which may be mentioned are: ethinyl, n-prop-2-in-1-yl, n-but-2-in-1-yl, n-pent-4-in-1-yl and n-hex-5-in-1-yl.

$(C_1–C_4)$-Alkoxy in the context of the invention represents a straight-chain or branched alkoxy radical having 1 to 4 carbon atoms. Examples which may be mentioned are: methoxy, ethoxy, n-propoxy, isopropoxy, t-butoxy, n-pentoxy and n-hexoxy. Methoxy and ethoxy are preferred.

$(C_5–C_8)$-Cycloalkyl in the context of the invention represents cyclopentyl, cyclohexyl, cycloheptyl or cyclooctyl. The following may preferably be mentioned are: cyclopentyl, cyclohexyl or cycloheptyl.

Halogen in the context of the invention in general represents fluorine, chlorine, bromine and iodine. Fluorine, chlorine and bromine are preferred. Fluorine and chlorine are particularly preferred.

Preferred salts in the context of the invention are physiologically acceptable salts of the compounds according to the invention.

Physiologically acceptable salts of the compounds according to the invention can be acid addition salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid; lactic acid, tartaric acid, citric acid, fumaric acid, maleic acid or benzoic acid.

Salts which may be mentioned are, however, also salts with customary bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyl-diisopropylamine, procaine, dibenzylamine, N-methylmorpholine, dihydroabietylamine, 1-ephenamine or methyl-piperidine.

Hydrates of the compounds according to the invention are stoichiometric compositions of the compounds or salts thereof with water.

Solvates of the compounds according to the invention are stoichiometric compositions of the compounds or salts thereof with solvent.

The compounds according to the invention can exist in stereoisomeric forms, which either behave as image and mirror image (enantiomers), or which do not behave as image and mirror image (diastereomers). The invention relates both to the enantiomers and diastereomers or their respective mixtures. Like the diastereomers, the racemic forms can be separated into the stereoisomerically uniform constituents in a known manner.

Preferred compounds of the general formula (I) are those where $R^1$ denotes phenyl whose meta and/or para positions are substituted up to three times identically or differently by radicals selected from the group consisting of $(C_1-C_4)$-alkyl, $(C_1-C_4)$-alkoxy and $-SO_2NR^{10}R^{11}$, and $R^2$, $R^3$, $R^4$, $R^5$, $R^6$, $R^7$, $R^{10}$, $R^{11}$ and L have the meaning indicated above.

The meta and para positions of the phenyl ring are understood as meaning those positions which are meta or para to the $CR^2R^3$ group. These positions can be illustrated by the following structural formula (Ic):

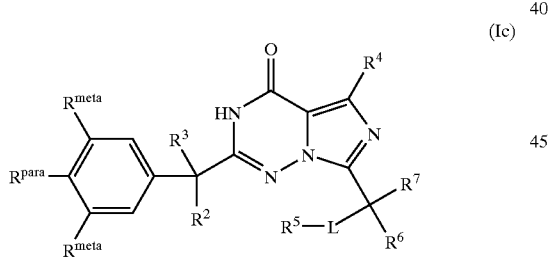

(Ic)

Particularly preferred compounds of the general formula (Ic) are those in which the para and one meta position of the phenyl radical are substituted, and the second meta position is unsubstituted.

Likewise, preferred compounds of the general formula (I) are those where $R^7$ denotes $(C_4-C_7)$-alkyl or $(C_4-C_7)$-alkenyl and $R^1$, $R^2$, $R^3$, $R^4$, $R^5$, $R^6$ and L have the meaning indicated above.

Very particularly preferred are compounds of the general formula (I), where $R^1$ denotes phenyl whose meta and/or para positions are substituted up to three times identically or differently by radicals selected from the group consisting of $(C_1-C_4)$-alkyl, $(C_1-C_4)$-alkoxy and $-SO_2NR^{10}R^{11}$, in which $R^{10}$ and $R^{11}$ independently of one another are hydrogen or $(C_1-C_4)$-alkyl, $R^2$ and $R^3$ denote hydrogen, $R^4$ denotes methyl or ethyl, $R^5$ denotes methyl, $R^6$ denotes hydrogen or methyl, L denotes carbonyl or hydroxymethanediyl, and $R^7$ denotes n-butyl, n-pentyl, n-hexyl or n-pent-4-en-1-yl.

A further aspect of the invention relates to a new preparation process for the compounds of the general formula (I), in which $R^1$, $R^2$, $R^3$, $R^4$, $R^5$, $R^6$, $R^7$ and L have the meaning indicated above, where

[A] a compound of the general formula (IIa),

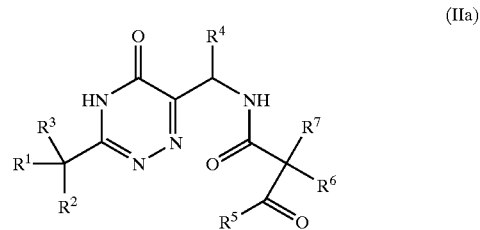

(IIa)

in which $R^1$, $R^2$, $R^3$, $R^4$, $R^5$, $R^6$ and $R^7$ have the meaning indicated in Claim 1, is reacted under suitable condensation conditions to give a compound of the general formula (Ia),

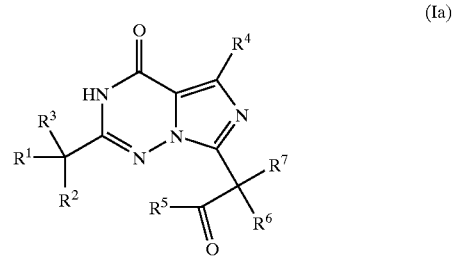

(Ia)

in which $R^1$, $R^2$, $R^3$, $R^4$, $R^5$, $R^6$ and $R^7$ have the meaning indicated in Claim 1, and then, if appropriate,

[B] is reduced under suitable conditions to give a compound of the general formula (Ib)

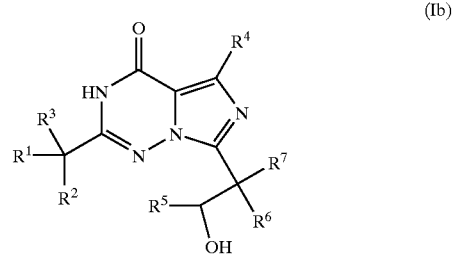

(Ib)

in which $R^1$, $R^2$, $R^3$, $R^4$, $R^5$, $R^6$ and $R^7$ have the meaning indicated in Claim 1.

The condensation according to reaction step [A] can be carried out by heating the compounds of the general formula (IIa) in the absence of a solvent or in the presence of an inert solvent, in particular of a solvent of the type which forms an azeotropic mixture with water, such as, for example, toluene or xylene, if appropriate in the presence of an acid catalyst and/or of a dehydrating agent. A suitable acid catalyst is, for example, hydrogen chloride and a dehydrating agent which can be used is, for example, acetyl chloride, phosphorus pentoxide or phosphorus oxychloride. The condensation is preferably carried out in an inert solvent in the presence of 1–10, preferably 3–7, equivalents of phosphorus oxychloride (cf. *Chem. Ind.* 1983, 331–335).

Suitable inert solvents for the condensation are the customary organic solvents which do not change under the reaction conditions. These include, for example, ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformamide, hexamethylphosphoramide, acetonitrile, acetone, dimethoxyethane or pyridine. It is likewise possible to use mixtures of the solvents mentioned. 1,2-Dichloroethane is preferred.

The reaction temperature can be varied within a relatively wide range. In general, the reaction is carried out in a range from −20° C. to 200° C., preferably from −20° C. to 90° C.

The process steps according to the invention are in general carried out at normal pressure. However, it is also possible to work at elevated pressure or at reduced pressure (e.g. in a range from 0.5 to 5 bar).

The reduction according to reaction step [B] can be carried out according to customary methods.

The reductions are in general carried out using hydrides or using boranes, diboranes or their complex compounds in inert solvents.

The reductions can also be carried out by means of hydrogen in water or in inert solvents such as alcohols, ethers or halogenohydrocarbons, or their mixtures, using catalysts such as Raney nickel, palladium, palladium on active carbon or platinum.

Preferably, the reductions are carried out using hydrides, such as complex borohydrides or aluminium hydrides. Particularly preferably, sodium borohydride, lithium borohydride, sodium cyanoborohydride, lithium aluminium hydride, sodium bis(2-methoxyethoxy)aluminium hydride or borane/tetrahydrofuran are employed here.

Suitable solvents here for the reduction are all solvents which do not change under the reaction conditions. These preferably include alcohols such as methanol, ethanol, n-propanol or isopropanol, or ethers such as diethyl ether, dioxane, tetrahydrofuran, glycol dimethyl ether, diethylene glycol dimethyl ether or amides such as hexamethylphosphoramide or dimethylformamide, or acetic acid. It is likewise possible to use mixtures of the solvents mentioned.

The reduction is in general carried out in a temperature range from −50° C. up to the respective boiling point of the solvent, preferably from −20° C. to +90° C., particularly preferably from −5° C. to 30° C.

If necessary, the compounds of the general formula (I) can be separated into the pure diastereomers and/or pure enantiomers. For example, chromatographic separation under normal-, medium- or high-pressure conditions on stationary phases such as, for example, silica gel or reversed phase-modified silica gels or chirally modified silica gels is suitable for this purpose. This is preferably carried out by the high-performance liquid chromatography (=HPLC) method using chiral stationary silica gel phases. Chiral polyamide/silica gel phases based on the monomers N-methacryloyl-L-leucine-d-menthylamide or N-methacryloyl-L-leucine-1-menthyl-amide are particularly suitable for the separation of the racemates (cf. EP-A-0 379 917).

It can also prove favourable to employ diastereomerically and/or enantiomerically pure compounds of the general formula (IIa) in reaction step [A] and/or to separate the compounds of the general formula (Ia) into the pure diastereomers and/or enantiomers, if appropriate, before carrying out reaction step [B].

It is likewise possible to carry out the reduction [B] diastereoselectively. For this purpose, the reduction is expediently carried out using hydrides, such as complex borohydrides or aluminium hydrides and also boranes in the presence of metal salts. Particularly preferred metal salts are those whose cations are capable of bidentate coordination, such as, for example, metals of the main groups IIa and IIIa or metals of the subgroups including the lanthanoids. Salts of Zn, Mn, Mg or Ca are particularly preferred. Anions which can be used are, for example, halides or acetates. The reaction is expediently carried out in an alcohol or a mixture of an alcohol and a further inert solvent. Mixtures of methanol or ethanol and dichloromethane are preferred. The reduction is in general carried out in a temperature range from −50° C. up to the respective boiling point of the solvent, preferably from −20° C. to +90° C., particularly preferably from −5° C. to 30° C.

The reduction is carried out, inter alia, using 1 to 20 equivalents of the reducing agent in the presence of 0.1 to 10 equivalents of metal salt. In a preferred embodiment, 0.2 to 3 equivalents of metal salt are used. Preferred reducing agents are, for example, sodium borohydride, lithium borohydride, sodium cyanoborohydride or zinc borohydride.

The intermediates of the general formula (II) are new.

A further aspect of the present invention therefore relates to the new compounds of the general formula (II),

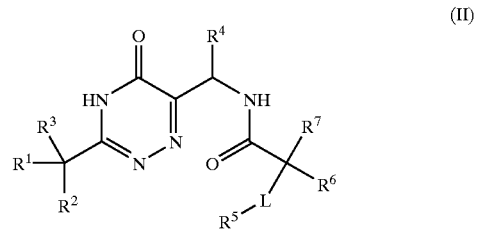

in which $R^1$, $R^2$, $R^3$, $R^4$, $R^5$, $R^6$, $R^7$ and L have the meaning indicated above, and their salts.

The compounds of the general formula (IIa) can be prepared, for example, according to known methods by the oxidation of corresponding compounds of the general formula (IIb),

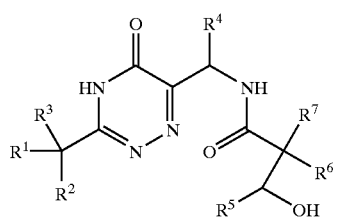

in which $R^1$, $R^2$, $R^3$, $R^4$, $R^5$, $R^6$ and $R^7$ have the meaning indicated in Claim 1, for example by Swern oxidation or Collins oxidation (for further oxidation methods also see March, J. M., "Advanced Organic Chemistry", 3rd Edition, John Wiley, New York, 1985, pp. 1057–1060 and literature cited therein).

The preparation of the compounds of the general formula (II) can be illustrated by way of example by the following synthesis scheme:

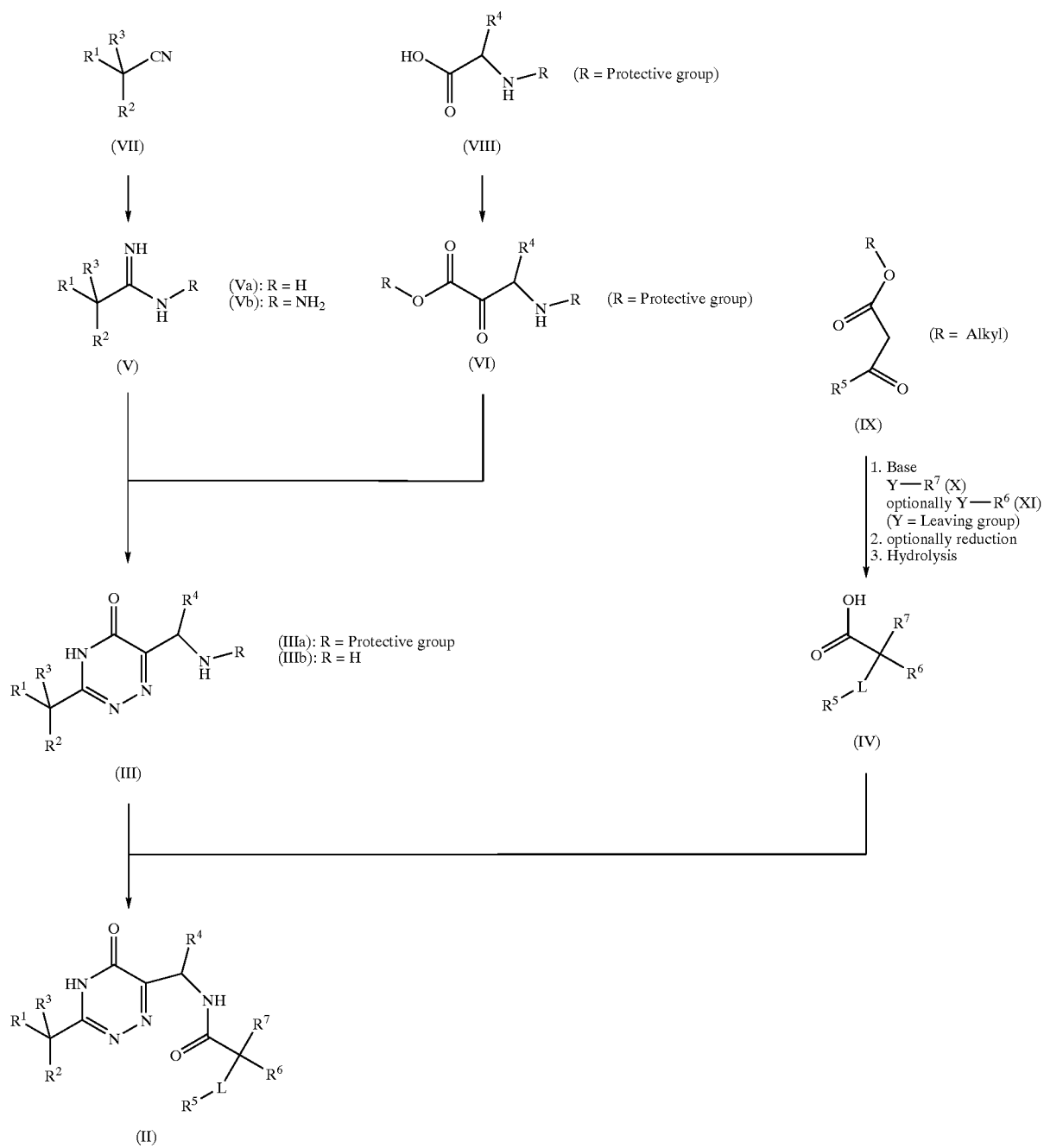

The compounds of the general formulae (III), (IV), (V), (VI), (VII), (VIII), (IX), (X) and (XI) are known or can be prepared by known processes.

According to this reaction scheme, the aminomethyltriazinones (IIIb) are condensed with the carboxylic acids (IV) under the conditions customary for the formation of amide bonds using a dehydrating reagent in an inert solvent, if appropriate in the presence of a base.

Suitable dehydrating reagents are carbodiimides, such as, for example, diisopropylcarbodiimide, dicyclohexylcarbodiimide (DCC) or N-(3-dimethylaminopropyl)-N'-ethylcarbodiimide hydrochloride (EDC) or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine, N-ethylmorpholine, N-methylmorpholine or N-methylpiperidine, and if appropriate in the presence of a catalyst such as N-hydroxysuccinimide or N-hydroxybenzotriazole (HOBT). The condensation with EDC is preferably carried out in the presence of NMM and HOBT.

Suitable solvents are the customary inert solvents described above. Dichloromethane is preferred.

The aminomethyltriazinones (IIIb) are obtainable by deprotection of the corresponding N-protected aminomethyltriazinones (IIIa), which in turn are accessible via cyclocondensation of the corresponding amidrazones (Vb) and α-keto esters (VI).

Suitable amino protective groups for the intermediates (IIIa), (VI) and (VIII) are, for example, acyl radicals, in particular the acetyl group. These groups can be cleaved into the N-protected aminomethyltriazinones (IIIa) under acidic conditions, for example by heating in hydrochloric acid.

The cyclocondensation to give the N-protected aminomethyltriazinones (IIIa) can be brought about by heating the individual components, the amidrazones (Vb) and α-keto esters (VI), in an alcoholic solvent, preferably by heating to reflux in ethanol.

The amidrazones (Vb) can be prepared by reaction of the corresponding amidines (Va) with, for example, hydrazine hydrate and are either isolated or employed in situ in the following reaction. The amidines (Va) are accessible from the corresponding nitriles (VII) according to customary methods, for example by reaction of the nitrites (VII) with ammonium chloride and a solution of trimethylaluminium in hexane firstly in a temperature range from −20° C. to room temperature, preferably at 0° C. and then at 60 to 100° C., preferably 70 to 90° C., and preferably at normal pressure.

The nitrites (VII) are known or can be prepared according to customary methods. For example, aryl-difluoro-acetonitriles can be prepared from arylacetonitriles or aryloxoacetonitriles (cf. *J. Org. Chem.* 1998, 63, 8052–8057 or *J. Fluorine Chem.* 1996, 76, 15–20).

The α-keto esters (VI) can be prepared from the corresponding N-protected α-amino acids (VIII), for example by reaction with ethyl oxalyl chloride.

The carboxylic acids (IV) are accessible by alkylation of the corresponding β-keto esters (IX) with the electrophiles (X) and if appropriate (XI), followed by ester hydrolysis and, if appropriate, reduction of the β-carbonyl function.

For alkylation, the β-ketoester (IX) is deprotonated for example using a base, preferably a hydride such as sodium hydride, in an inert solvent such as, for example, tetrahydrofuran in a temperature range from preferably 0° C. to room temperature and, after isolation or in situ, treated with a solution of the electrophile (X) or (XI) in, preferably, 1,3-dimethyltetrahydro-2-(1H)-pyrimidone with addition of a catalytic amount of potassium iodide. If $R^6$ is not hydrogen, the alkylation can be repeated using a second electrophile after the monoalkylation product has optionally been isolated.

The leaving group Y in the electrophile (X) or (XI) is preferably a halogen, particularly preferably bromine.

The β-carbonyl function can be reduced according to the conditions described above for reaction step [B].

The hydrolysis of the ester to the carboxylic acid (IV) is carried out according to customary conditions, in the case of the methyl or ethyl ester preferably using sodium or potassium hydroxide solution.

Substituents, for example in $R^1$, can be introduced via the starting materials, such as, for example, via the nitrile (VII), but can also be introduced or modified in a later process stage.

Thus the substituent $-SO_2NR^{10}R^{11}$, for example, can be introduced into $R^1$ by chlorosulphonating an appropriate N-protected aminomethyltriazinone (IIIa) with chlorosulphonic acid and then further reacting it with an appropriate amine $HNR^{10}R^{11}$ to give the corresponding sulphonamide.

This can be illustrated by the following reaction scheme:

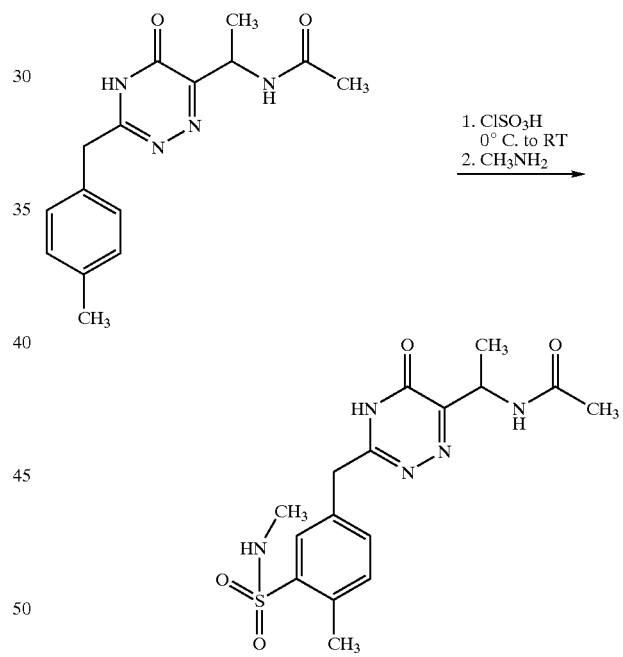

The compounds according to the invention show an unforeseeable, valuable spectrum of pharmacological action: they preferably inhibit PDE 2, and/or exhibit a favourable pharmacokinetic profile.

The inhibition of PDE 2 leads to a differentiated increase in cGMP. The differentiating action is additionally determined by the distribution of the isoenzymes in the tissue.

The compounds according to the invention moreover intensify the action of substances, such as, for example, EDRF (endothelium-derived relaxing factor) and ANP (atrial natriuretic peptide), which increase the cGMP level.

Because of their selective PDE 2 inhibition, the compounds according to the invention are particularly suitable for improving perception, concentration power, learning power or memory power, in particular after cognitive disorders, such as occur, for example, in situations/illnesses/syndromes such as mild cognitive impairment, age-associated learning and memory disorders, age-associated memory losses, vascular dementia, craniocerebral trauma, stroke, dementia which occurs after strokes (post-stroke dementia), post-traumatic craniocerebral trauma, general concentration disorders, concentration disorders in children with learning and memory problems, Alzheimer's disease, vascular dementia, dementia with Lewy bodies, dementia with degeneration of the frontal lobes including Pick's disease, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff psychosis.

The compounds according to the invention are generally suitable for the treatment and/or prophylaxis of dementia.

The active compound can act systemically and/or locally. For this purpose, it can be administered in a suitable manner, such as, for example, orally, parenterally, pulmonarily, nasally, sublingually, lingually, buccally, rectally, transdermally, conjunctivally, otically or as an implant.

For these administration routes, the active compound can be administered in suitable administration forms.

For oral administration, known administration forms releasing the active compound rapidly and/or in modified form are suitable, such as, for example, tablets (non-coated and coated tablets, e.g. enteric coatings), capsules, sugar-coated tablets, granules, pellets, powders, emulsions, suspensions and solutions.

The parenteral administration can take place with circumvention of an absorption step (intravenous, intraarterial, intracardiac, intraspinal or intralumbar) or with involvement of an absorption (intramuscular, subcutaneous, intracutaneous, percutaneous, or intraperitoneal). For parenteral administration, suitable administration forms are, inter alia, injection and infusion preparations in the form of solutions, suspensions, emulsions, lyophilizates and sterile powders.

For the other administration routes, for example, inhalation pharmaceutical forms (inter alia powder inhalers, nebulizers), nasal drops/solutions, sprays; tablets or capsules to be applied lingually, sublingually or buccally, suppositories, ear and eye preparations, vaginal capsules, aqueous suspensions (lotions, shake lotions), lipphilic suspensions, ointments, creams, milk, pastes, dusting powder or implants are suitable.

The active compounds can be converted into the administration forms mentioned in a known manner. This takes place using inert non-toxic, pharmaceutically suitable excipients. These include, inter alia, vehicles (e.g. microcrystalline cellulose), solvents (e.g. liquid polyethylene glycols), emulsifiers (e.g. sodium dodecylsulphate), dispersants (e.g. polyvinylpyrrolidone), synthetic and natural biopolymers (e.g. albumin), stabilizers (e.g. antioxidants such as ascorbic acid), colourants (e.g. inorganic pigments such as iron oxides) or taste and/or odour corrigents.

In general, it has proved advantageous in the case of parenteral administration to administer amounts of approximately 0.001 to 30 mg/kg, preferably approximately 0.01 to 10 mg/kg, of body weight to achieve effective results. In the case of oral administration, the amount is approximately 0.01 to 100 mg/kg, preferably approximately 0.1 to 30 mg/kg, of body weight.

In spite of this, it may be necessary, if appropriate, to deviate from the amounts mentioned, namely depending on the body weight, route of application, individual behaviour towards the active compound, manner of preparation and time or interval at which administration takes place.

Measurement of the PDE Inhibition

The cGMP-stimulable PDE (PDE 2), the cGMP-inhibitable PDE (PDE 3) and the cAMP-specific PDE (PDE 4) were isolated either from porcine or bovine heart myocardium. The $Ca^{2+}$ calmodulin-stimulable PDE 1 was isolated from porcine aorta, porcine brain or preferably from bovine aorta. The cGMP-specific PDE (PDE 5) was preferably obtained from porcine small intestine, porcine aorta, human blood platelets and preferably from bovine aorta. Purification was carried out by anion exchange chromatography on mono $Q^R$ Pharmacia essentially according to the method of Hoey, M; Houslay, M. D., *Biochem. Pharmacol.* 1990, 40, 193–202 and Lugman et al. *Biochem. Pharmacol.* 1986, 35, 1743–1751.

The enzyme activity was determined in a test batch of 100 $\mu$l in 20 mM tris/HCl buffer pH 7.5 which contains 5 mM $MgCl_2$, 0.1 mg/ml of bovine serum albumin and either 800 Bq of [$^3$H]-cAMP or [$^3$H]-cGMP. The final concentration of the corresponding nucleotides is $10^{-6}$ mol/l. The reaction is started by addition of the enzyme and the amount of enzyme is proportioned such that about 50% of the substrate are reacted during the incubation time of 30 min. In order to test the cGMP-stimulable PDE 2, [$^3$H]-cAMP is used as a substrate and $10^{-6}$ mol/l of non-labelled cGMP is added to the batch. In order to test the Ca calmodulin-dependent PDE 1, additionally $CaCl_2$ 1 $\mu$M and calmodulin 0.1 $\mu$M and are added to the reaction batch. The reaction is stopped by addition of 100 $\mu$l of acetonitrile which contains 1 mM cAMP and 1 mM AMP. 100 $\mu$l of the reaction batch are separated on the HPLC and the cleavage products are determined quantitatively online using a flow-through scintillation counter. The substance concentration at which the reaction rate is decreased by 50% is measured. In addition, the phosphodiesterase [$^3$H] cAMP SPA enzyme assay and the phosphodiesterase [$^3$H] cGMP SPA enzyme assay from Amersham Life Sciences were used for testing. The test was carried out according to the experimental protocol indicated by the manufacturer.

The activity of the test substances on PDE 2 was determined using the [$^3$H] cAMP Scintillation Proximity Assay (SPA) kit (TRKQ7090) from Amersham International (Little Chalfont, England) or on PDE1 and PDE5 using the [$^3$H] cGMP Scintillation Proximity Assay (SPA) Kit (TRKQ7100) from Amersham International (Little Chalfont, England).

Test substances were dissolved in 100% DMSO (10 mM), and this solution was further diluted with $H_2O$ (highest final concentration in the test: 10 $\mu$M). For the prestimulation of the PDE 2, cGMP is additionally added (final concentration in the test: $10^{-6}$ M). The enzyme is diluted in PDE buffer (20 mM TRIS/HCl, 5 mM $MgCl_2$, 0.1 mg/ml of albumin, pH 7.5). The following volumes per hole are pipetted into a 96-hole plate (Wallac, 1450-401): 10 $\mu$l of substance solution (at the 100% value 10 $\mu$l of $H_2O$), 10 $\mu$l of cGMP ($10^{-5}$ M), 70 $\mu$l of [$^3$H]-cAMP test mixture (see kit), 10 $\mu$l of enzyme (at the 0 value no enzyme, instead of this +10 $\mu$l of $H_2O$) at the start of the reaction. After incubation at 30° C. for 15 min, the reaction was stopped using 50 $\mu$l of SPA bead solution (see kit), and the plate was sealed with a film and shaken for 30 seconds. After the beads had settled (about 15 min), the plate was measured in a beta counter.

For the measurement of PDE 1, calmodulin $10^{-7}$ M and $CaCl_2$ 1 $\mu$M were added to the reaction batch. The PDE 5 was measured using the [$^3$H] cGMP SPA Assay.

Under the conditions indicated above the working examples inhibit the PDE 2 with $IC_{50}$ values of less than 1 µm.

Measurement of the Increase in the Intracellular Neuronal cGMP Concentration in Cell Cultures PDE 2 inhibitors increase the intracellular neuronal cGMP concentration after prestimulation of the guanylate cyclase using $10^{-4}$ M sodium nitroprusside (SNP) in primary rat brain cell cultures.

Rat embryos were decapitated and the heads were transferred to preparation dishes. The scalp and cranium were removed, and the exposed brains were transferred to a further Petri dish. With the aid of a binocular microscope and two pairs of forceps, hippocampi were isolated from the cortex and cooled to 4° C. using ice. This preparation and the isolation of the hippocampal neurons were then carried out according to a standard protocol using the papain dissociation system (Worthington Biochemical Corporation, Lakewood, N.J. 08701, USA) (Huettner et al. *J. Neurosci.* 1986, 6, 3044–3060). The mechanically isolated neurons were cultured under standard conditions (37° C., 5% $CO_2$) to 150,000 cells/hole in 200 µl of neurobasal medium/hole (neurobasal; Gibco/BRL; 2 mM L-glutamine; in the presence of penicillin/streptomycin) for 7 days in 96-hole plates (pretreated with poly-D-lysine 100 µg/ml for 20 min). After 7 days, the medium was removed and the cells were washed with HBS buffer (Gibco/BRL). Subsequently, 100 µl each of SNP solution and 100 µl of the racemate of Example 1 (dissolved in 100% DMSO beforehand: 10 mM) were added in HBS to the cells such that the final concentration of SNP was 100 mM and that of the racemate of Example 1 was as indicated in FIG. 1 and the mixture was incubated at 37° C. for 20 min. The cells were then lysed in 200 µl of lysis buffer (cGMP kit code RPN 226; from Amersham Pharmacia Biotech.) and the cGMP concentration was measured according to the instructions of the manufacturer. All measurements were carried out in triplicate. Statistical analysis was carried out using Prism Software Version 2.0 (GraphPad Software Inc., San Diego, Calif. USA; *** p<0.001).

Object Recognition Test

The object recognition test is a memory test. It measures the ability of rats (and mice) to differentiate between known and unknown objects and is therefore suitable for the determination of the memory-improving action of the compounds according to the invention.

The test is carried out as described (Blokland et al. *NeuroReport* 1998, 9, 4205–4208; Ennaceur, A., Delacour, J., *Behav. Brain Res.* 1988, 31, 47–59; Ennaceur, A., Meliani, K., *Psychopharmacology* 1992, 109, 321–330; Prickaerts, et al. *Eur. J. Pharmacol.* 1997, 337, 125–136).

In a first passage, a rat in an otherwise empty relatively large observation arena is confronted with two identical objects. The rat will extensively examine, i.e. sniff and touch, both objects. In a second passage, after an interval of 24 hours, the rat is again tested in the observation arena. One of the known objects is now replaced by a new, unknown object. When a rat recognizes the known object, it will especially examine the unknown object. After 24 hours, a rat, however, has normally forgotten which object it has already examined in the first passage, and will therefore inspect both objects equally intensively. The administration of a substance having learning- and memory-improving action will lead to a rat recognizing the object already seen 24 hours beforehand, in the first passage, as known. It will examine the new, unknown object in greater detail than the already known one. This memory power is expressed in a discrimination index. A discrimination index of zero means that the rat examines both objects, the old and the new one, for the same length of time; i.e. it has not recognized the old object and reacts to both objects as if they were both unknown and new. A discrimination index of greater than zero means that the rat has inspected the new object for longer than the old one; i.e. the rat has recognized the old object.

Definitions of Terms

Chromatography, if not mentioned otherwise, was carried out on silica gel Si 60. In the case of flash chromatography, the described conditions were normally followed (cf. Still J. Org. Chem.).

If not described otherwise, the reactions were carried out under argon and, where necessary, under anhydrous conditions.

HPLC=high-pressure liquid chromatography
MS=mass spectrometry
NMR=nuclear magnetic resonance spectroscopy
LC-MS=liquid chromatography combined with mass spectrometry
MeOH=methanol
DMSO=dimethyl sulphoxide
THF=tetrahydrofuran
of th.=of theory

STARTING COMPOUNDS

EXAMPLE 1A

N-Acetylalanine

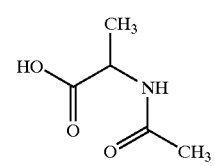

134 g (1.50 mol) of DL-alanine are introduced into acetic acid and treated dropwise with 230 g (2.25 mol) of acetic anhydride. The mixture is additionally stirred at 100° C. for 2 h to complete the reaction and the solvent is then stripped off in vacuo. The solid obtained is suspended in ethyl acetate and filtered off with suction. For purification, the solid is washed several times with diethyl ether.

Yield: 162 g (82.6% of th.)

$^1$H-NMR (methanol-$d_4$): δ=1.38 (d, 3H), 1.97 (s, 3H), 4.37 (q, 1H).

EXAMPLE 2A 2-(Acetylamino)butanoic acid

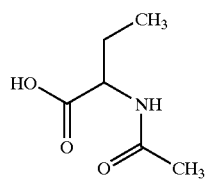

163 g (1.58 mol) of 2-aminobutyric acid are reacted analogously to Example 1A with 242 g (2.37 mol) of acetic anhydride to give 2-(acetylamino)butanoic acid.

Yield: 220 g (95.9% of th.)

$^1$H-NMR (CD$_3$OD): δ=0.97 (t, 3H), 1.65–1.93 (m, 2H), 1.99 (s, 3H), 4.29 (q, 1H).

EXAMPLE 3A 2-(4-Methylphenyl)ethanamidine hydrochloride

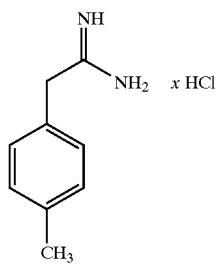

10.8 g (201 mmol) of ammonium chloride are suspended in 200 ml of dry toluene and the suspension is cooled to 0° C. 100 ml of a 2M solution of trimethylaluminium in hexane are added dropwise and the mixture is stirred at room temperature until the evolution of gas is complete. After addition of 13.2 g (100 mmol) of 4-methylbenzyl cyanide, the reaction mixture is stirred overnight at 80° C. (bath). The cooled reaction mixture is treated with ice-cooling with 35 ml of methanol and then stirred at room temperature for a further 1 h. The solid is then first filtered off with suction, and the filter cake is washed several times with methanol. The filtrate is concentrated, the residue is resuspended in dichloromethane/methanol 10/1 and the insoluble solid is separated off. The filtrate is then again evacuated from the solvent in vacuo.

Yield: 16.4 g (88.1% of th.)

$^1$H-NMR (methanol-d$_4$): δ=2.35 (s, 3H), 3.77 (s, 2H), 7.21–7.29 (m, 4H).

EXAMPLE 4A 2-(4-Methoxyphenyl)ethanamidine hydrochloride

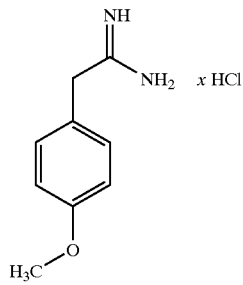

Analogously to Example 3A, starting from 21.4 g (400 mmol) of ammonium chloride, 200 ml of a 2M solution of trimethylaluminium in hexane and 29.4 g (200 mmol) of 4-methoxybenzyl cyanide, 28.5 g (71.3% of th.) of 2-(4-methoxyphenyl)ethanamidine hydrochloride are obtained.

Melting point: 126° C.

EXAMPLE 5A 2-(3,4-Dimethoxyphenyl)ethanamidine hydrochloride

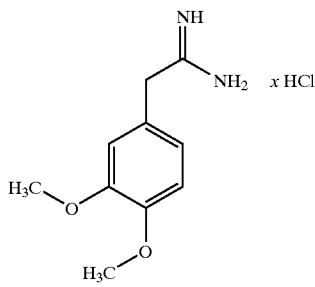

Analogously to Example 3A, starting from 72.5 g (1.35 mol) of ammonium chloride, 672 ml of a 2M solution of trimethylaluminium in hexane and 120 g (677 mmol) of 3,4-dimethoxybenzyl cyanide, 112 g (71.7% of th.) of 2-(3,4-dimethoxyphenyl)ethanamidine hydrochloride are obtained.

$^1$H-NMR (DMSO-d$_6$): δ=3.62 (s, 2H), 3.74 (s, 3H), 3.76 (s, 3H), 6.92–7.14 (m, 3H).

EXAMPLE 6A

Ethyl 3-(acetylamino)-2-oxobutanoate

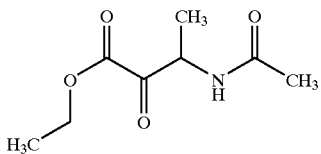

10.65 g (81.2 mmol) of acetylalanine (Example 1A) are taken up in 150 ml of tetrahydrofuran and heated under reflux with 19.3 g (244 mmol) of pyridine and a spatula tipful of N,N-dimethylaminopyridine. At boiling heat, 22.2 g (162 mmol) of ethyl oxalyl chloride are added dropwise. The mixture is then heated at reflux until the evolution of gas can no longer be observed. After cooling, the batch is added to ice water and the organic phase is extracted in ethyl acetate. The dried organic phase is concentrated and, dissolved directly in ethanol, reacted further.

EXAMPLE 7A

N-{1-[3-(4-Methylbenzyl)-5-oxo-4,5-dihydro-1,2,4-triazin-6-yl]ethyl}acetamide

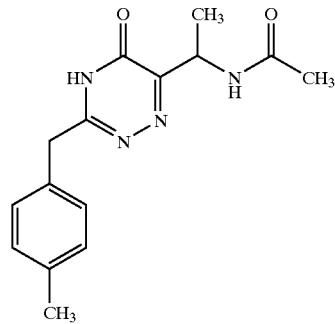

10 g (54.2 mmol) of 2-(4-methylphenyl)ethanamidine hydrochloride (Example 3A) are taken up in 100 ml of ethanol and treated with 3.25 g (65.0 mmol) of hydrazine hydrate. The mixture is stirred for 45 min, then the compound of Example 6A is added. It is then stirred for 4 h at 80° C. (bath) and overnight at room temperature. The substance is purified by flash chromatography, preliminary fractions first being separated off using ethyl acetate. The product is eluted with dichloromethane/methanol 30/1.

Yield: 5.63 g (36.3% of th.)

$^1$H-NMR (methanol-$d_4$): δ=1.40 (d, 3H), 1.93 (s, 3H), 2.29 (s, 3H), 3.85 (s, 2H), 5.12 (q, 1H), 7.12–7.23 (m, 4H).

EXAMPLE 8A 6-(1-Aminoethyl)-3-(4-methylbenzyl)-1,2,4-triazin-5(4H)-one

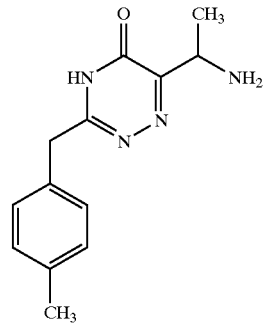

20 g (69.9 mmol) of N-{1-[3-(4-methylbenzyl)-5-oxo-4,5-dihydro-1,2,4-triazin-6-yl]ethyl}acetamide (Example 7A) are stirred under reflux in 200 ml of 2 N hydrochloric acid for 18 h. The cooled mixture is then neutralized using 6 N NaOH and evaporated to dryness in vacuo. The residue is suspended in methanol and the salt is separated off. The concentrated filtrate is flash-chromatographed using dichloromethane/methanol 20/1 and 5/1.

Yield: 8 g (46.9% of th.)

$^1$H-NMR (methanol-$d_4$): δ=1.50 (d, 3H), 2.20 (s, 3H), 3.84 (s, 2H), 4.52 (q, 1H), 7.03 (d, 2H), 7.13 (d, 2H).

EXAMPLE 9A

N-{1-[3-(4-Methoxybenzyl)-5-oxo-4,5-dihydro-1,2,4-triazin-6-yl]ethyl}acetamide

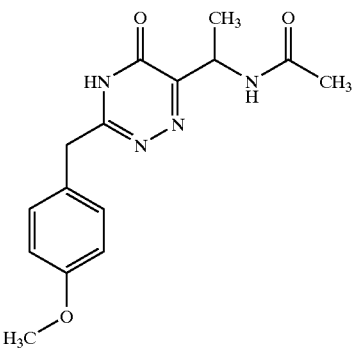

Analogously to Example 7A, 5.1 g (25.4 mmol) of 2-(4-methoxyphenyl)ethanamidine hydrochloride (Example 4A) are reacted with 1.53 g (30.5 mmol) of hydrazine hydrate and 7.14 g (38.1 mol) of ethyl 3-(acetylamino)-2-oxobutanoate (Example 6A) to give N-{1-[3-(4-methoxybenzyl)-5-oxo-4,5-dihydro-1,2,4-triazin-6-yl]ethyl}acetamide.

Yield: 2.97 g (38.7% of th.)

$^1$H-NMR (methanol-$d_4$): δ=1.44 (d, 3H), 1.99 (s, 3H), 3.78 (s, 3H), 3.91 (s, 2H), 5.23 (q, 1H), 6.90 (d, 2H), 7.28 (d, 2H).

EXAMPLE 10A 6-(1-Aminoethyl)-3-(4-methoxybenzyl)-1,2,4-triazin-5(4H)-one

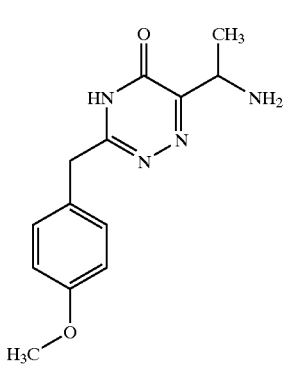

Analogously to Example 8A, 17 g (56.2 mmol) of N-{1-[3-(4-methoxybenzyl)-5-oxo-4,5-dihydro-1,2,4-triazin-6-yl]ethyl}acetamide (Example 9A) are reacted to give 6-(1-aminoethyl)-3-(4-methoxybenzyl)-1,2,4-triazin-5(4H)-one.

Yield: 5 g (34.2% of th.)

$^1$H-NMR (methanol-d$_4$): δ=1.55 (d, 3H), 3.74 (s, 3H), 3.84 (s, 2H), 4.51 (q, 1H), 6.83 (d, 2H), 7.24 (d, 2H).

EXAMPLE 11A

N-{1-[3-(3,4-Dimethoxybenzyl)-5-oxo-4,5-dihydro-1,2,4-triazin-6-yl]ethyl}acetamide

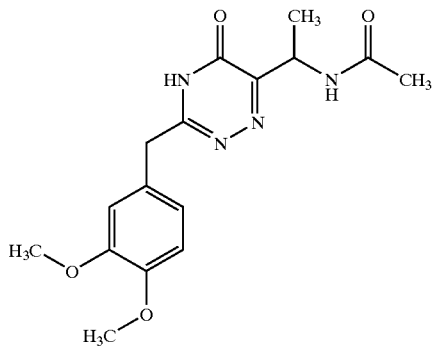

Analogously to Example 7A, 20.0 g (86.7 mmol) of 2-(3,4-dimethoxyphenyl)ethanamidine hydrochloride (Example 5A) are reacted with 5.21 g (104 mmol) of hydrazine hydrate and 24.3 g (130 mmol) of ethyl 3-(acetylamino)-2-oxobutanoate (Example 6A) to give N-{1-[3-(3,4-dimethoxybenzyl)-5-oxo-4,5-dihydro-1,2,4-triazin-6-yl]ethyl}acetamide.

Yield: 15.5 g (77.5% of th.)

$^1$H-NMR (methanol-d$_4$): δ=1.40 (d, 3H), 1.95 (s, 3H), 3.78 (s, 3H), 3.81 (s, 3H), 3.82 (s, 2H), 5.16 (q, 1H), 6.86–6.97 (m, 3H).

EXAMPLE 12A 6-(1-Aminoethyl)-3-(3,4-dimethoxybenzyl)-1,2,4-triazin-5(4H)-one

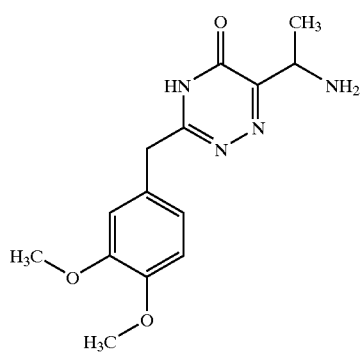

Analogously to Example 8A, 23 g of N-{1-[3-(3,4-dimethoxybenzyl)-5-oxo-4,5-dihydro-1,2,4-triazin-6-yl]ethyl}acetamide (Example 11A) are reacted to give 6-(1-aminoethyl)-3-(3,4-dimethoxybenzyl)-1,2,4-triazin-5(4H)-one.

Yield: 10.1 g (50.4% of th.)

$^1$H-NMR (methanol-d$_4$): δ=1.55 (d, 3H), 3.78 (s, 3H), 3.80 (s, 3H), 3.83 (s, 2H), 4.52 (q, 1H), 6.83–6.98 (m, 3H).

EXAMPLE 13A

Sodium (2E)-4-methoxy-4-oxo-2-buten-2-olate

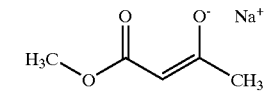

60 g of a 30% strength sodium hydride suspension in mineral oil (744 mmol of NaH) are suspended in 250 ml of dry THF in an inert gas atmosphere. 86.4 g (744 mmol) of methyl acetoacetate in 200 ml of THF are slowly added dropwise, the resulting hydrogen being led directly into the waste air. After dropwise addition has taken place, the mixture is stirred at reflux for half an hour and then cooled. The solvent is stripped off in vacuo and the residual solid is washed with diethyl ether.

Yield: 81.9 g (79.7% of th.)

Melting point: the substance decomposes at 200° C.

EXAMPLE 14A

Methyl 2-acetylhexanoate

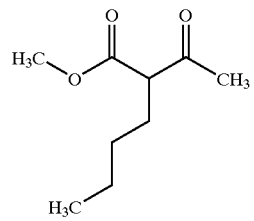

30 g (217 mmol) of sodium (2E)-4-methoxy-4-oxo-2-buten-2-olate (Example 13A) suspended in 1,3-dimethyltetrahydro-2(1H)-pyrimidone and 1.24 g (7.5 mmol) of potassium iodide are treated dropwise with 29.8 g (217 mmol) of butyl bromide and the mixture is stirred at 80° C. for 1 h under reflux. The cooled mixture is then added to ice water and extracted with diethyl ether. The ether phase is washed with sodium thiosulphate solution, dried, concentrated and chromatographed. The eluent used is cyclohexane having an increasing ethyl acetate content.

Yield: 11.6 g (30.9% of th.)

$^{1}$H-NMR (CDCl$_{3}$): δ=0.90 (t, 3H), 1.21–1.41 (m, 4H), 1.80–1.90 (m, 2H), 2.22 (s, 3H), 3.41 (t, 1H), 3.74 (s, 3H).

EXAMPLE 15A

2-Acetylhexanoic acid

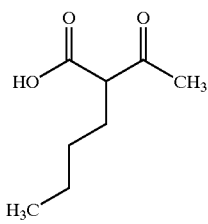

3.08 g (17.9 mmol) of methyl 2-acetylhexanoate (Example 14A) is dissolved in 10 ml of dioxane and cooled to 0° C. 7.00 ml of a 3.5 M potassium hydroxide solution are added with cooling. After a reaction time of 5 h, the batch is concentrated, treated with 20 ml of ethyl acetate and 20 ml of water and extracted with shaking. The water phase is recovered, cooled to 0° C. and slowly treated with 1 N hydrochloric acid until a pH of 1 is reached. The mixture is then extracted with dichloromethane. The dichloromethane phase is dried and directly reacted further without concentrating.

EXAMPLE 16A

Methyl 2-acetylheptanoate

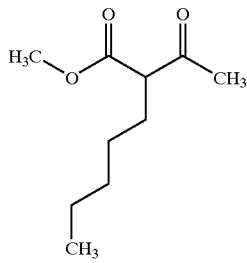

Analogously to Example 14A, 30 g (217 mmol) of sodium (2E)-4-methoxy-4-oxo-2-buten-2-olate (Example 13A) and 1.24 g (7.5 mmol) of potassium iodide are reacted with 32.8 g (217 mmol) of n-pentyl bromide to give methyl 2-acetylheptanoate.

Yield: 10.5 g (26.0% of th.)

$^{1}$H-NMR (CDCl$_{3}$): δ=0.89 (t, 3H), 1.20–1.38 (m, 6H), 1.84 (m, 2H), 2.22 (s, 3H), 3.42 (t, 1H), 3.73 (s, 3H).

EXAMPLE 17A

2-Acetylheptanoic acid

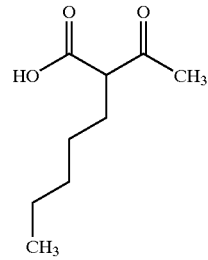

Analogously to Example 15A, 900 mg (5.23 mmol) of methyl 2-acetylheptanoate (Example 16A) are reacted with 2.5 ml of a 3.5 M potassium hydroxide solution to give 2-acetylheptanoic acid in dichloromethane.

EXAMPLE 18A

Methyl 2-acetyloctanoate

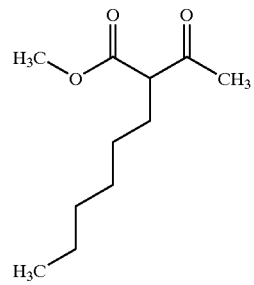

Analogously to Example 14A, 30 g (217 mmol) of sodium (2E)-4-methoxy-4-oxo-2-buten-2-olate (Example 13A) and 1.24 g (7.5 mmol) of potassium iodide are reacted with 37.7 g (228 mmol) of hexyl bromide to give methyl 2-acetyloctanoate.

Yield: 16.03 g (36.8% of th.)

$^{1}$H-NMR (CDCl$_{3}$): δ=0.89 (t, 3H), 1.19–1.39 (m, 8H), 1.84 (m, 2H), 2.22 (s, 3H), 3.42 (t, 1H), 3.73 (s, 3H).

EXAMPLE 19A

2-Acetyloctanoic acid

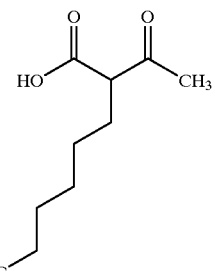

Analogously to Example 15A, 3.16 g (15.8 mmol) of methyl 2-acetyloctanoate (Example 18A) are reacted with 7 ml of a 3.5 M potassium hydroxide solution to give 2-acetyloctanoic acid in dichloromethane.

EXAMPLE 20A

Methyl 2-acetyl-6-heptenoate

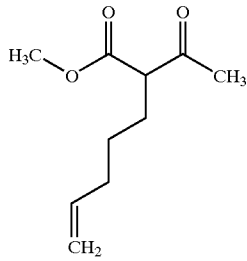

Analogously to Example 14A, 10 g (72.4 mmol) of sodium (2E)-4-methoxy-4-oxo-2-buten-2-olate (Example 13A) and 0.4 g (2.41 mmol) of potassium iodide are reacted with 10.8 g (72.4 mmol) of 1-bromopentene to give methyl 2-acetyl-6-heptenoate.

Yield: 5.0 g (37.5% of th.)

$^1$H-NMR (CDCl$_3$: δ=1.33–1.47 (m, 2H), 1.79–1.94 (m, 2H), 1.99–2.15 (m, 2H), 2.23 (s, 3H), 3.43 (t, 1H), 3.74 (s, 3H), 4.93–5.08 (m, 2H), 5.67–5.88 (m, 1H).

EXAMPLE 21A

Methyl 2-(1-hydroxyethyl)-6-heptenoate

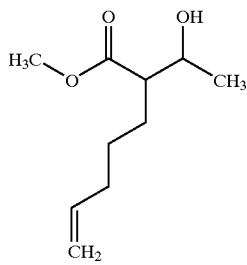

5.00 g (27.1 mmol) of methyl 2-acetyl-6-heptenoate (Example 20A) are introduced into 50 ml of methanol and ice-cooled. 0.56 g (14.9 mmol) of sodium borohydride are added in portions and the mixture is stirred for a further 1 h. The batch is then evacuated from the solvent, taken up in diethyl ether and washed with 1 N hydrochloric acid. The organic phase is dried, concentrated and flash-chromatographed using the eluent petroleum ether/ethyl acetate 10/1.

Yield: 4.9 g (96.9% of th.)

$^1$H-NMR (CDCl$_3$, diastereomer mixture): δ=1.17–1.25 (d, 3H), 1.33–1.48 (m, 2H), 1.55–1.71 (m, 2H), 2.00–2.14 (m, 2H), 2.29–2.49 (m, 1H), 3.73 (s, 3H), 3.85–3.99 (m, 1H), 4.91–5.07 (m, 2H), 5.67–5.90 (m, 1H).

EXAMPLE 22A 2-(1-Hydroxyethyl)-6-heptenoic acid

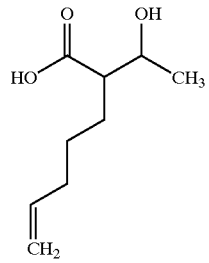

Analogously to Example 15A, 4.80 g (25.8 mmol) of methyl 2-(1-hydroxyethyl)-6-heptenoate (Example 21A) are reacted with 39.0 ml of a 1 M sodium hydroxide solution to give 2-(1-hydroxyethyl)-6-heptenoic acid.

EXAMPLE 23A

2-Acetyl-N-{1-[3-(4-methylbenzyl)-5-oxo-4,5-dihydro-1,2,4-triazin-6-yl]ethyl}hexanamide

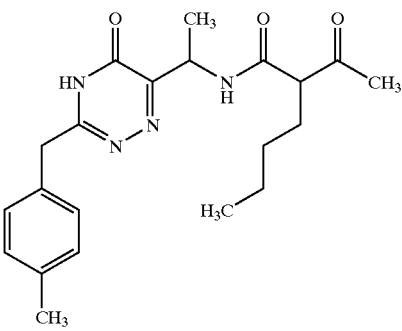

The amount of 2-acetylhexanoic acid in dichloromethane from Example 15A is treated with 2.3 g (17.0 mmol) of 1-hydroxy-1H-benzotriazole and 3.44 g (34 mmol) of 4-methylmorpholine and cooled to −20° C. After addition of 3.26 g (17.0 mmol) of N'-(3-dimethylaminopropyl)-N-ethylcarbodiimide hydrochloride, the mixture is stirred for 30 min. The cooling bath is removed in the course of this. 1.60 g (6.55 mmol) of 6-(1-aminoethyl)-3-(4-methylbenzyl)-1,2,4-triazin-5(4H)-one (Example 8A) are then added after fresh cooling to −20° C. and the mixture is stirred overnight while warming to room temperature. For work-up, the dichloromethane phase is washed with 1 N potassium hydrogensulphate solution and then with saturated sodium hydrogencarbonate solution. The dried organic phase is concentrated and chromatographed using the eluent dichloromethane/methanol 100/1 to 30/1.

Yield: 1.69 g (67.1% of th.)

$^1$H-NMR (methanol-d$_4$, diastereomer mixture): δ=0.83–0.93 (m, 3H), 1.16–1.40 (m, 4H), 1.45 (d, 3H), 1.74 (m, 2H), 2.17 (s, 3H), 2.30 (s, 3H), 3.70 (m, 1H), 3.85 (s, 2H), 5.12 (m, 1H), 7.10–7.24 (m, 4H).

EXAMPLE 24A

2-Acetyl-N-{1-[3-(4-methylbenzyl)-5-oxo-4,5-dihydro-1,2,4-triazin-6-yl]ethyl}heptanamide

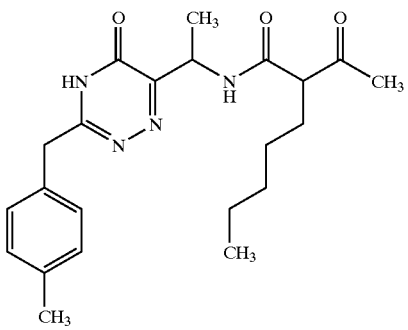

The amount of 2-acetylheptanoic acid in dichloromethane from Example 17A is reacted analogously to Example 23A with 680 mg (5.0 mmol) of 1-hydroxy-1H-benzotriazole, 1.52 g (15.0 mmol) of 4-methylmorpholine, 960 mg (5.0 mmol) of N'-(3-dimethylaminopropyl)-N-ethylcarbodiimide hydrochloride and 1.22 g (5.00 mmol) of 6-(1-aminoethyl)-3-(4-methylbenzyl)-1,2,4-triazin-5(4H)-one (Example 8A) to give 2-acetyl-N-{1-[3-(4-methylbenzyl)-5-oxo-4,5-dihydro-1,2,4-triazin-6-yl]ethyl}heptanamide.

Yield: 533 mg (26.8% of th.)

$^1$H-NMR (methanol-$d_4$, diastereomer mixture): δ=0.82–0.93 (m, 3H), 1.19–1.34 (m, 6H), 1.44 (d, 3H), 1.74 (m, 2H), 2.17 (s, 3H), 2.30 (s, 3H), 3.43 (m, 1H), 3.85 (s, 2H), 5.13 (m, 1H), 7.11–7.24 (m, 4H).

EXAMPLE 25A

2-Acetyl-N-{1-[3-(4-methylbenzyl)-5-oxo-4,5-dihydro-1,2,4-triazin-6-yl]ethyl}octanamide

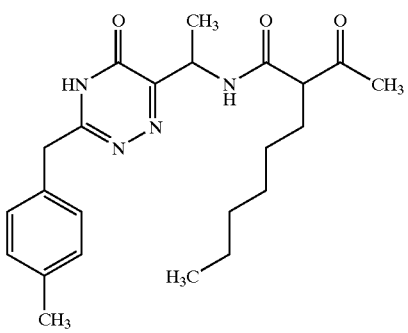

The amount of 2-acetyloctanoic acid in dichloromethane from Example 19A is reacted analogously to Example 23A with 2.14 g (15.8 mmol) of 1-hydroxy-1H-benzotriazole, 1.90 g (18.8 mmol) of 4-methylmorpholine, 3.03 g (15.8 mmol) of N'-(3-dimethylaminopropyl-N-ethylcarbodiimide hydrochloride and 3.80 mg (15.6 mmol) of 6-(1-aminoethyl)-3-(4-methylbenzyl)-1,2,4-triazin-5(4H)-one (Example 8A) to give 2-acetyl-N-{1-[3-(4-methylbenzyl)-5-oxo-4,5-dihydro-1,2,4-triazin-6-yl]ethyl}octanamide.

Yield: 909 mg (14.2% of th.)

LC-MS: retention time 3.89 and 3.94 min., m/z 413.3 [M+H]$^+$

LC parameters: soln. A acetonitrile+0.1% formic acid
Soln. B water+0.1% formic acid
Column oven 40° C.;
Column symmetry C18 50 mm×2.1 mm

| | Gradient: | | |
| --- | --- | --- | --- |
| Time | % A | % B | Flow |
| 0 | 10 | 90 | 0.5 |
| 4 | 90 | 10 | 0.5 |
| 6 | 90 | 10 | 0.5 |
| 6.1 | 10 | 90 | 1.0 |
| 7.5 | 10 | 90 | 0.5 |
| 9 | 90 | 10 | 0.8 |

EXAMPLE 26A

2-Acetyl-N-{1-[3-(4-methoxybenzyl)-5-oxo-4,5-dihydro-1,2,4-triazin-6-yl]ethyl}heptanamide

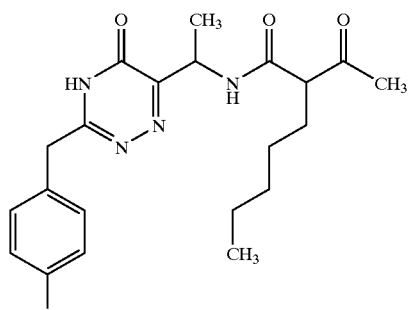

1.29 g (6.91 mmol) of methyl 2-acetylheptanoate (Example 16A) are hydrolysed to 2-acetylheptanoic acid according to Example 17A. The acid in 20 ml of dichloromethane is reacted analogously to Example 23A with 903 mg (6.90 mmol) of 1-hydroxy-1H-benzotriazole, 2.02 g (20 mmol) of 4-methylmorpholine, 1.32 g (6.90 mmol) of N'-(3-dimethylaminopropyl)-N-ethylcarbodiimide hydrochloride and 890 mg (3.4 mmol) of 6-(1-aminoethyl)-3-(4-methoxybenzyl)-1,2,4-triazin-5(4H)-one (Example 10A) to give 2-acetyl-N-{1-[3-(4-methoxybenzyl)-5-oxo-4,5-dihydro-1,2,4-triazin-6-yl]ethyl}heptanamide.

Yield: 357 mg (25.3% of th.)

$^1$H-NMR (CDCl$_3$, diastereomer mixture): δ=0.78–0.94 (m, 3H), 1.19–1.34 (m, 6H), 1.46 (d, 3H), 1.83 (m, 2H), 2.20 and 2.24 (each s, 3H), 3.31 (m, 1H), 3.81 (s, 3H), 3.94 (s, 2H), 5.11 (m, 1H), 6.83–7.31 (m, 4H, under CHCl$_3$ signal).

EXAMPLE 27A

2-Acetyl-N-{1-[3-(4-methoxybenzyl)-5-oxo-4,5-dihydro-1,2,4-triazin-6-yl]ethyl}octanamide

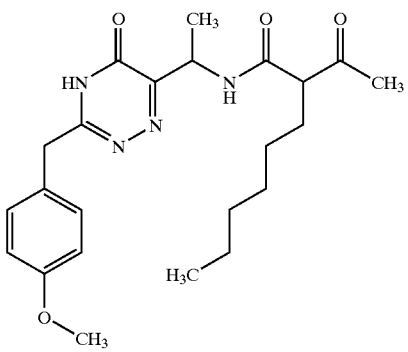

1.18 g (5.91 mmol) of methyl 2-acetyloctanoate (Example 18A) are hydrolysed to 2-acetyloctanoic acid according to Example 19A. The acid in 20 ml of dichloromethane is reacted analogously to Example 23A with 800 mg (5.90 mmol) of 1-hydroxy-1H-benzotriazole, 1.66 g (16.4 mmol) of 4-methylmorpholine, 1.13 g (5.9 mmol) of N'-(3-dimethylaminopropyl)-N-ethylcarbodiimide hydrochloride and 900 mg (3.5 mmol) of 6-(1-aminoethyl)-3-(4-methoxybenzyl)-1,2,4-triazin-5(4H)-one (Example 10A) to give 2-acetyl-N-{1-[3-(4-methoxybenzyl)-5-oxo-4,5-dihydro-1,2,4-triazin-6-yl]ethyl}octanamide.

Yield: 722 mg (48.7% of th.)

$^1$H-NMR (CDCl$_3$, diastereomer mixture): δ=0.80–0.90 (m, 3H), 1.16–1.33 (m, 8H), 1.46 (d, 3H), 1.84 (m, 2H), 2.20 and 2.23 (each s, 3H), 3.32 (m, 1H), 3.79 (s, 3H), 3.94 (s, 2H), 5.13 (m, 1H), 6.85–7.30 (m, 4H, under CHCl$_3$ signal).

EXAMPLE 28A

2-Acetyl-N-{1-[3-(3,4-dimethoxybenzyl)-5-oxo-4,5-dihydro-1,2,4-triazin-6-yl]ethyl}octanamide

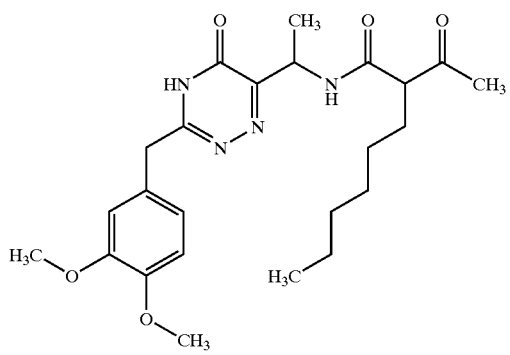

601 g (3.0 mmol) of methyl 2-acetyloctanoate (Example 18A) are hydrolysed to 2-acetyloctanoic acid according to Example 19A. The acid in 20 ml of dichloromethane is reacted analogously to Example 23A with 1.08 g (8.0 mmol) of 1-hydroxy-1H-benzotriazole, 1.62 g (16.0 mmol) of 4-methylmorpholine, 1.53 g (8.0 mmol) of N'-(3-dimethylaminopropyl)-N-ethylcarbodiimide hydrochloride and 870 mg (3.0 mmol) of 6-(1-aminoethyl)-3-(3,4-methoxybenzyl)-1,2,4-triazin-5(4H)-one (Example 12A) to give 2-acetyl-N-{1-[3-(3,4-dimethoxybenzyl)-5-oxo-4,5-dihydro-1,2,4-triazin-6-yl]ethyl}octanamide.

Yield: 149 mg (10.8% of th.)

$^1$H-NMR (DMSO-d$_6$, diastereomer mixture): δ=0.79–0.90 (m, 3H), 1.08–1.34 (m, 11H), 1.59 (m, 2H), 2.08 and 2.09 (each s, 3H), 3.41 (m, 1H), 3.72 (s, 3H), 3.74 (s, 3H), 3.76 (s, 2H), 4.98 (m, 1H), 6.79–6.99 (m, 3H).

EXAMPLE 29A

N-{1-[3-(3,4-Dimethoxybenzyl)-5-oxo-4,5-dihydro-1,2,4-triazin-6-yl]ethyl}-2-(1-hydroxyethyl)-6-heptenamide

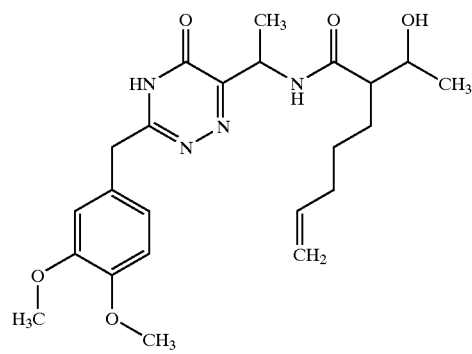

742 mg (4.31 mmol) of 2-(1-hydroxyethyl)-6-heptenoic acid (Example 22A) are reacted analogously to Example 23A with 580 mg (4.31 mmol) of 1-hydroxy-1H-benzotriazole, 870 mg (8.61 mmol) of 4-methylmorpholine, 830 mg (4.31 mmol) of N'-(3-dimethylaminopropyl)-N-ethylcarbodiimide hydrochloride and 500 mg (1.72 mmol) of 6-(1-aminoethyl)-3-(3,4-dimethoxybenzyl)-1,2,4-triazin-5(4H)-one (Example 12A) to give N-{1-[3-(3,4-dimethoxybenzyl)-5-oxo-4,5-dihydro-1,2,4-triazin-6-yl]ethyl}-2-(1-hydroxyethyl)-6-heptenamide.

Yield: 285 mg (37.2% of th.)

$^1$H-NMR (methanol-d$_4$, diastereomer mixture): δ=1.10–1.19 (m, 3H), 1.25–1.79 (m, 7H), 1.96–2.10 (m, 2H), 2.15–2.26 (m, 1H), 3.66–3.85 (m, 9H), 4.90–5.02 (m, 2H), 5.10–5.21 (m, 1H), 5.67–5.85 (m, 1H), 6.85–6.99 (m, 3H).

EXAMPLE 30A

2-Acetyl-N-{1-[3-(3,4-dimethoxybenzyl)-5-oxo-4,5-dihydro-1,2,4-triazin-6-yl]ethyl}-6-heptenamide

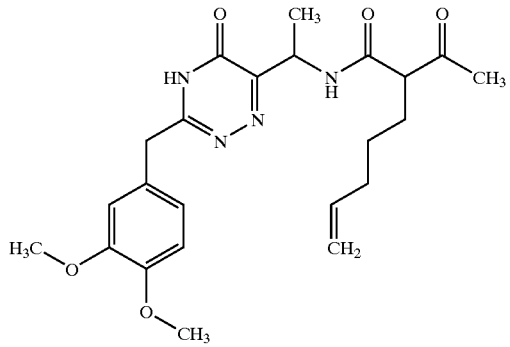

100 mg (0.76 mmol) of oxalyl chloride in 5 ml of dichloromethane are treated dropwise at −70° C. with 130 mg (1.64 mmol) of dimethyl sulphoxide. The mixture is stirred at −70° C. for 30 min, then 280 mg (0.63 mmol) of N-{1-[3-(3,4-dimethoxybenzyl)-5-oxo-4,5-dihydro-1,2,4-triazin-6-yl]ethyl}-2-(1-hydroxyethyl)-6-heptenamide (Example 29A) are added. After a further 30 min, during which the temperature in the batch rises to about −60° C., 320 mg (3.15 mmol) of triethylamine are added and the cooling bath is then removed. If the batch temperature is warmed almost to room temperature, 10 ml of water are added and the phases are separated after stirring briefly. The dried organic phase is chromatographed in dichloromethane/methanol 50/1.

Yield: 175 mg (55.9% of th.)

$^1$H-NMR (methanol-d$_4$, diastereomer mixture): δ=1.27–1.38 (m, 2H), 1.46 (d, 3H), 1.71–1.80 (m, 2H), 1.99–2.21 (m, 2H), 2.17 (s, 3H), 3.44 (m, 1H), 3.78–3.86 (m, 8H), 4.87–5.03 (m, 2H), 5.09–5.17 (m, 1H), 5.68–5.84 (m, 1H), 6.85–6.99 (m, 3H).

WORKING EXAMPLES

EXAMPLE 1

7-(1-Acetylpentyl)-5-methyl-2-(4-methylbenzyl)imidazo[5,1-f][1,2,4]triazin-4(3H)-one

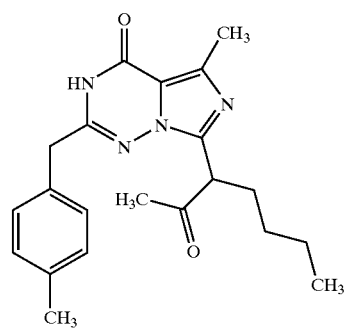

1.66 g (4.31 mmol) of 2-acetyl-N-{1-[3-(4-methylbenzyl)-5-oxo-4,5-dihydro-1,2,4-triazin-6-yl]ethyl}hexanamide (Example 23A) in 20 ml of dichloroethane are treated with 3.31 g (21.6 mmol) of phosphorus oxychloride and the mixture is stirred at 100° C. under reflux for 1 h. The cooled mixture is neutralized with saturated sodium hydrogencarbonate solution and the solvent is stripped off. The product is chromatographed using dichloromethane/methanol 70/1.

Yield: 1.58 g (quant.)

R$_f$ value (dichloromethane/methanol 10/1): 0.58

$^1$H-NMR (400 MHz, methanol-d$_4$): δ=0.90 (t, 3H), 1.26–1.40 (m, 4H), 1.92–2.27 (m, 2H), 2.29 (s, 3H), 2.32 (s, 3H), 2.71 (s, 3H), 3.88 (s, 2H), 4.74 (m, 1H), 7.17 (d, 2H), 7.24 (d, 2H).

EXAMPLE 2

7-(1-Acetylhexyl)-5-methyl-2-(4-methylbenzyl)imidazo[5,1-f][1,2,4]triazin-4(3H)-one

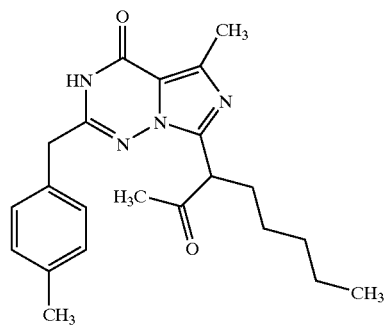

Analogously to Example 1, 520 mg (1.30 mmol) of 2-acetyl-N-{1-[3-(4-methylbenzyl)-5-oxo-4,5-dihydro-1,2,4-triazin-6-yl]ethyl}heptanamide (Example 24A) and 1.99 g (13.0 mmol) of phosphorus oxychloride are reacted to give 7-(1-acetylhexyl)-5-methyl-2-(4-methylbenzyl)imidazo[5,1-f][1,2,4]triazin-4(3H)-one.

Yield: 495 mg (quant.)

R$_f$ value (dichloromethane/methanol 10/1): 0.56

$^1$H-NMR (300 MHz, methanol-d$_4$): δ=0.88 (t, 3H), 1.18–1.38 (m, 6H), 1.93–2.24 (m, 2H), 2.28 (s, 3H), 2.32 (s, 3H), 2.71 (s, 3H), 3.89 (s, 2H), 4.75 (m, 1H), 7.17 (d, 2H), 7.25 (d, 2H).

EXAMPLE 3

7-(1-Acetylheptyl)-5-methyl-2-(4-methylbenzyl)imidazo[5,1-f][1,2,4]triazin-4(3H)-one

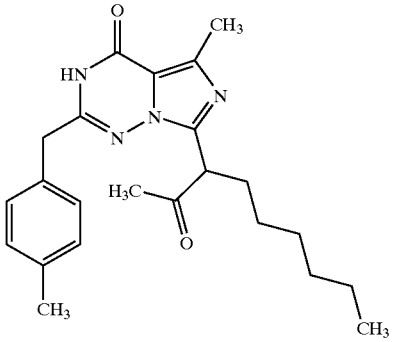

Analogously to Example 1, 910 mg (2.20 mmol) of 2-acetyl-N-{1-[3-(4-methylbenzyl)-5-oxo-4,5-dihydro-1,2,4-triazin-6-yl]ethyl}octanamide (Example 25A) and 1.65 g (10.7 mmol) of phosphorus oxychloride are reacted to give 7-(1-acetylheptyl)-5-methyl-2-(4-methylbenzyl)imidazo[5,1-f][1,2,4]triazin-4(3H)-one.

Yield: 870 mg (quant.)

$R_f$ value (dichloromethane/methanol 10/1): 0.64

$^1$H-NMR (400 MHz, methanol-$d_4$): δ=0.88 (t, 3H), 1.15–1.38 (m, 8H), 1.93–2.24 (m, 5H, s at 2.17), 2.31 (s, 3H), 2.64 (s, 3H), 3.86 (s, 2H), 4.55 (m, 1H), 7.16 (d, 2H), 7.24 (d, 2H).

EXAMPLE 4

7-(1-Acetylhexyl)-2-(4-methoxybenzyl)-5-methylimidazo[5,1-f][1,2,4]triazin-4(3H)-one

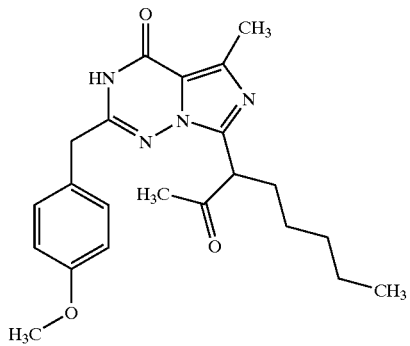

Analogously to Example 1, 340 mg (0.82 mmol) of 2-acetyl-N-{1-[3-(4-methoxybenzyl)-5-oxo-4,5-dihydro-1,2,4-triazin-6-yl]ethyl}heptanamide (Example 26A) and 540 g (3.50 mmol) of phosphorus oxychloride are reacted to give 7-(1-acetylhexyl)-2-(4-methoxybenzyl)-5-methylimidazo[5,1-f][1,2,4]triazin-4(3H)-one.

Yield: 218 mg (67.0% of th.)

$R_f$ value (dichloromethane/methanol 10/1): 0.56

$^1$H-NMR (400 MHz, methanol-$d_4$): δ=0.85 (t, 3H), 1.18–1.35 (m, 6H), 1.95–2.12 (m, 5H, s at 2.03), 2.53 (s, 3H), 3.75 (s, 2H), 3.77 (s, 3H), 4.27 (m, 1H), 6.88 (d, 2H), 7.25 (d, 2H).

EXAMPLE 5

7-(1-Acetylheptyl)-2-(4-methoxybenzyl)-5-methylimidazo[5,1-f][1,2,4]triazin-4(3H)-one

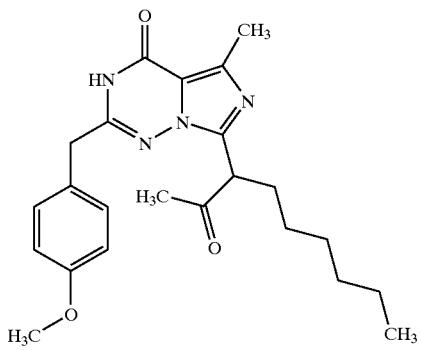

Analogously to Example 1, 710 mg (1.65 mmol) of 2-acetyl-N-{1-[3-(4-methoxybenzyl)-5-oxo-4,5-dihydro-1,2,4-triazin-6-yl]ethyl}octanamide (Example 27A) and 1.23 g (8.00 mmol) of phosphorus oxychloride are reacted to give 7-(1-acetylheptyl)-2-(4-methoxybenzyl)-5-methylimidazo[5,1-f][1,2,4]triazin-4(3H)-one.

Yield: 507 mg (75.1% of th.)

$R_f$ value (dichloromethane/methanol 10/1): 0.47

$^1$H-NMR (400 MHz, methanol-$d_4$): δ=0.86 (t, 3H), 1.15–1.35 (m, 8H), 1.95–2.13 (m, 5H, s at 2.03), 2.53 (s, 3H), 3.77 (s, 3H), 3.79 (s, 2H), 4.29 (m, 1H), 6.88 (d, 2H), 7.25 (d, 2H).

EXAMPLE 6

7-(1-Acetylheptyl)-2-(3,4-dimethoxybenzyl)-5-methylimidazo[5,1-f][1,2,4]triazin-4(3H)-one

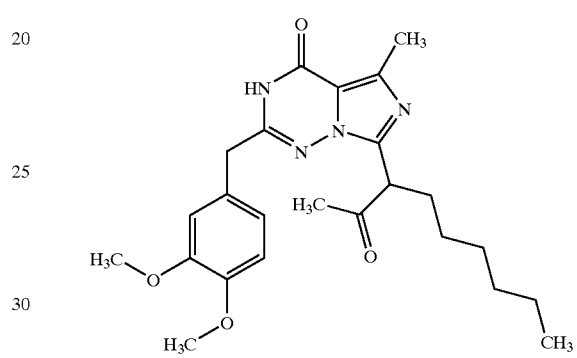

Analogously to Example 1, 150 mg (0.32 mmol) of 2-acetyl-N-{1-[3-(3,4-dimethoxybenzyl)-5-oxo-4,5-dihydro-1,2,4-triazin-6-yl]ethyl}octanamide (Example 28A) and 250 g (1.61 mmol) of phosphorus oxychloride are reacted to give 7-(1-acetylheptyl)-2-(3,4-dimethoxybenzyl)-5-methylimidazo[5,1-f][1,2,4]triazin-4(3H)-one.

Yield: 80 mg (55.9% of th.)

$R_f$ value (dichloromethane/methanol 10/1): 0.62

$^1$H-NMR (400 MHz, methanol-$d_4$): δ=0.85 (t, 3H), 1.15–1.32 (m, 8H), 1.99–2.14 (m, 5H, s at 2.03), 2.54 (s, 3H), 3.78 (s, 2H), 3.80 (s, 3H), 3.82 (s, 3H) 4.27 (m, 1H), 6.87–6.97 (m, 3H).

EXAMPLE 7

7-(1-Acetyl-5-hexenyl)-2-(3,4-dimethoxybenzyl)-5-methylimidazo[5,1-f][1,2,4]-triazin-4(3H)-one

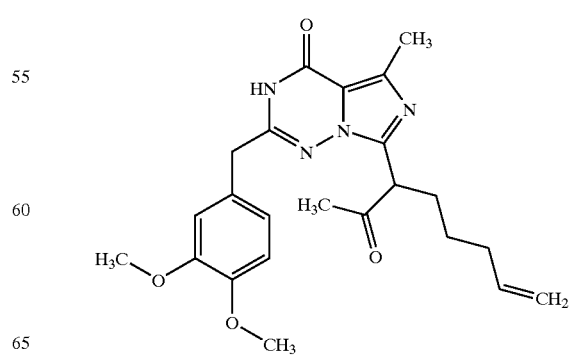

Analogously to Example 1, 160 mg (0.36 mmol) of 2-acetyl-N-{1-[3-(3,4-di-methoxybenzyl)-5-oxo-4,5-dihydro-1,2,4-triazin-6-yl]ethyl}-6-heptenamide (Example 30A) and 0.06 g (0.36 mmol) of phosphorus oxychloride are reacted to give 7-(1-acetyl-5-hexenyl)-2-(3,4-dimethoxybenzyl)-5-methylimidazo[5,1-f][1,2,4]triazin-4(3H)-one.

Yield: 115 mg (74.9% of th.)

$R_f$ value (dichloromethane/methanol 10/1): 0.58

$^1$H-NMR (400 MHz, methanol-$d_4$): δ=1.22–1.37 (m, 2H), 1.97–2.15 (m, 7H, s at 2.02), 2.54 (s, 3H), 3.78 (s, 2H), 3.82 (s, 3H), 3.83 (s, 3H) 4.28 (m, 1H), 4.87–4.98 (m, 2H), 5.68–5.80 (m, 1H), 6.89–6.95 (m, 3H).

EXAMPLE 8

7-[1-(1-Hydroxyethyl)pentyl]-5-methyl-2-(4-methylbenzyl)imidazo[5,1-f][1,2,4]-triazin-4(3H)-one

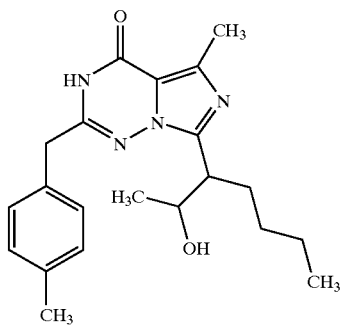

200 mg (0.55 mmol) of 7-(1-acetylpentyl)-5-methyl-2-(4-methylbenzyl)imidazo[5,1-f][1,2,4]triazin-4(3H)-one (Example 1) are dissolved in 5 ml of ethanol and treated in portions with 38 mg (1.00 mmol) of sodium borohydride. The batch is stirred at room temperature for 1 h, then it is neutralized with a few drops of 2 N hydrochloric acid. The solvent is stripped off in vacuo, then the residue is chromatographed using the eluent dichloromethane/methanol 40/1.

Yield: 46 mg (22.9% of th.)

$R_f$ value (dichloromethane/methanol 10/1): 0.44

$^1$H-NMR (400 MHz, methanol-$d_4$, diastereomer mixture): δ=0.82 (t, 3H), 0.91–1.37 (m, 7H), 1.68–2.09 (m, 2H), 2.31 (s, 3H), 2.53 and 2.54 (each s, 3H), 3.37 (m, 1H), 3.79 (s, 2H), 3.97–4.13 (m, 1H), 7.10–7.26 (m, 4H).

EXAMPLE 9

7-[1-(1-Hydroxyethyl)hexyl]-5-methyl-2-(4-methylbenzyl)imidazo[5,1-f][1,2,4]-triazin-4(3H)-one

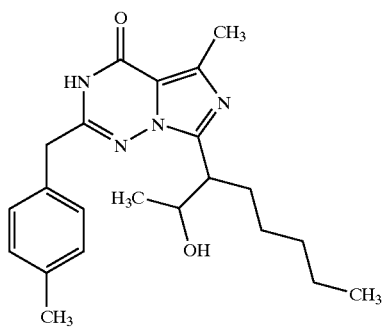

100 mg (0.26 mmol) of 7-(1-acetylhexyl)-5-methyl-2-(4-methylbenzyl)-imidazo[5,1-f][1,2,4]triazin-4(3H)-one (Example 2) are reacted analogously to Example 8 with 15 mg (0.39 mmol) of sodium borohydride to give 7-[1-(1-hydroxyethyl)hexyl]-5-methyl-2-(4-methylbenzyl)-imidazo[5,1-f][1,2,4]triazin-4(3H)-one.

Yield: 43 mg (42.8% of th.)

$R_f$ value (dichloromethane/methanol 10/1): 0.44

$^1$H-NMR (400 MHz, methanol-$d_4$, diastereomer mixture): δ=0.81–0.91 (m, 3H), 1.05 and 1.12 (each d, 3H), 1.18–1.36 (m, 6H), 1.80–2.08 (m, 2H), 2.31 (s, 3H), 2.62 and 2.67 (each s, 3H), 3.44–3.57 (m, 1H) 3.84 and 3.86 (each s, 2H), 3.97–4.16 (m, 1H), 7.16 (d, 2H), 7.25 (d, 2H).

EXAMPLE 10

7-[1-(1-Hydroxyethyl)heptyl]-5-methyl-2-(4-methylbenzyl)imidazo[5,1-f][1,2,4]triazin-4(3H)-one

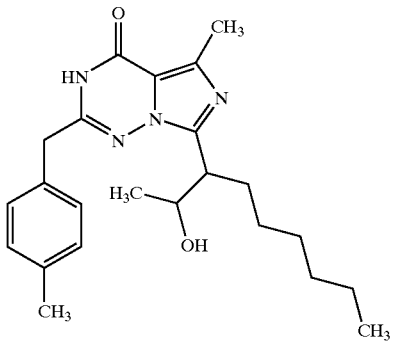

100 mg (0.25 mmol) of 7-(1-acetylheptyl)-5-methyl-2-(4-methylbenzyl)-imidazo[5,1-f][1,2,4]triazin-4(3H)-one (Example 3) are reacted analogously to Example 8 with 10 mg (0.25 mmol) of sodium borohydride to give 7-[1-(1-hydroxyethyl)heptyl]-5-methyl-2-(4-methylbenzyl)-imidazo[5,1-f][1,2,4]triazin-4(3H)-one.

Yield: 33 mg (32.8% of th.)

$R_f$ value (dichloromethane/methanol 10/1): 0.54

$^1$H-NMR (400 MHz, methanol-$d_4$, diastereomer mixture): δ=0.80–0.94 (m, 3H), 1.05 and 1.12 (each d, 3H), 1.18–1.38 (m, 8H), 1.78–2.09 (m, 2H), 2.31 (s, 3H), 2.62 and 2.67 (each s, 3H), 3.44–3.57 (m, 1H) 3.84 and 3.88 (each s, 2H), 3.97–4.15 (m, 1H), 7.16 (d, 2H), 7.25 (d, 2H).

EXAMPLE 11

7-[1-(1-Hydroxyethyl)heptyl]-2-(4-methoxybenzyl)-5-methylimidazo[5,1-f][1,2,4]triazin-4(3H)-one

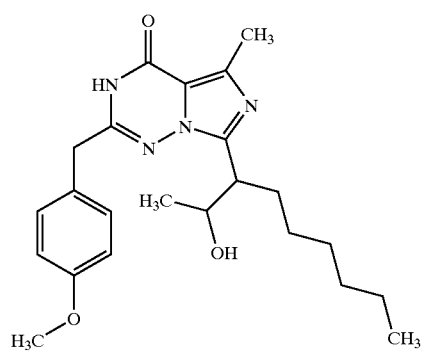

100 mg (0.24 mmol) of 7-(1-acetylheptyl)-2-(4-methoxybenzyl)-5-methylimidazo[5,1-f][1,2,4]triazin-4(3H)-one (Example 5) are reacted analogously to Example 8 with 17 mg (0.45 mmol) of sodium borohydride to give 7-[1-(1-hydroxyethyl)heptyl]-2-(4-methoxybenzyl)-5-methylimidazo[5,1-f][1,2,4]triazin-4(3H)-one.

Yield: 14 mg (13.9% of th.)

$^1$H-NMR (400 MHz, methanol-$d_4$, diastereomer mixture): δ=0.84 (t, 3H), 0.84–1.37 (m, 11H), 1.67–2.09 (m, 2H), 2.53 and 2.54 (each s, 3H), 3.32–3.41 (m, 1H) 3.76–3.78 (m, 5H), 3.98–4.13 (m, 1H), 6.88 (d, 2H), 7.26 (d, 2H).

EXAMPLE 12

2-(3,4-Dimethoxybenzyl)-7-[1-(1-hydroxyethyl)-5-hexenyl]-5-methylimidazo[5,1-f][1,2,4]triazin-4(3H)-one

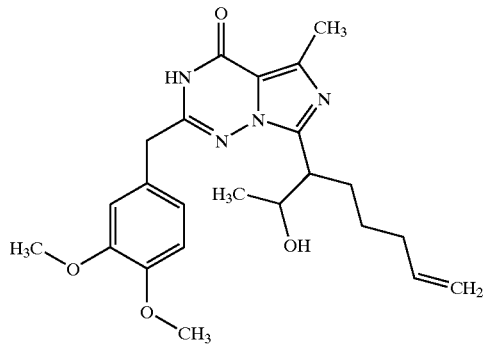

90 mg (0.20 mmol) of 7-(1-acetyl-5-hexenyl)-2-(3,4-dimethoxybenzyl)-5-methylimidazo[5,1-f][1,2,4]triazin-4(3H)-one (Example 7) are reacted analogously to Example 8 with 8 mg (0.20 mmol) of sodium borohydride to give 2-(3,4-dimethoxybenzyl)-7-[1-(1-hydroxyethyl)-5-hexenyl]-5-methylimidazo[5,1-f][1,2,4]triazin-4(3H)-one.

Yield: 43 mg (50.4% of th.)

$R_f$ value (dichloromethane/methanol 10/1): 0.40

$^1$H-NMR (400 MHz, methanol-$d_4$, diastereomer mixture): δ=0.92–1.25 (m, 5H, each d at 0.94 and 1.19), 1.70–2.12 (m, 4H), 2.54 (s, 3H), 3.34–3.42 (m, 1H), 3.76–3.84 (m, 8H), 3.98–4.13 (m, 1H) 4.85–4.94 (m, 2H), 5.64–5.76 (m, 1H), 6.87–6.98 (m, 3H).

What is claimed is:

1. A compound of the general formula (I),

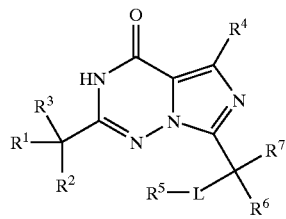

(I)

in which
R$^1$ denotes phenyl which can be substituted up to three times identically or differently by radicals selected from the group consisting of ($C_1$–$C_4$)-alkyl, ($C_1$–$C_4$)-alkoxy, halogen, cyano, —NHCOR$^8$, —NHSO$_2$R$^9$, —SO$_2$NR$^{10}$R$^{11}$, —SO$_2$R$^{12}$, and —NR$^{13}$R$^{14}$, in which
R$^8$, R$^{10}$, R$^{11}$, R$^{13}$ and R$^{14}$ independently of one another are hydrogen or ($C_1$–$C_4$)-alkyl,
and
R$^9$ and R$^{12}$ independently of one another are ($C_1$–$C_4$)-alkyl,
or
R$^{10}$ and R$^{11}$ together with the adjacent nitrogen atom form an azetidin-1-yl, pyrrol-1-yl, piperid-1-yl, azepin-1-yl, 4-methyl-piperazin-1-yl or morpholin-1-yl radical,
or
R$^{13}$ and R$^{14}$ together with the adjacent nitrogen atom form an azetidin-1-yl, pyrrol-1-yl, piperid-1-yl, azepin-1-yl, 4-methyl-piperazin-1-yl or morpholin-1-yl radical,
R$^2$ and R$^3$ independently of one another denote hydrogen or fluorine,
R$^4$ denotes ($C_1$–$C_4$)-alkyl,
R$^5$ denotes ($C_1$–$C_3$)-alkyl,
R$^6$ denotes hydrogen or methyl,
R$^7$ denotes ($C_1$–$C_{10}$)-alkyl, ($C_2$–$C_{10}$)-alkenyl or ($C_2$–$C_{10}$)-alkinyl, and
L denotes carbonyl or hydroxymethanediyl,
and salts thereof.

2. The compound according to claim 1, where R$^1$ denotes phenyl, whose meta and/or para positions are substituted up to three times identically or differently by radicals selected from the group consisting of ($C_1$–$C_4$)-alkyl, ($C_1$–$C_4$)-alkoxy and —SO$_2$NR$^{10}$R$^{11}$, and R$^{10}$ and R$^{11}$ have the meaning indicated in claim 1.

3. The compound according to claim 1 or 2, where R$^7$ denotes ($C_4$–$C_7$)-alkyl or ($C_4$–$C_7$)-alkenyl.

4. The compound according to claim 1,
where
R$^1$ denotes phenyl whose meta and/or para positions are substituted up to three times identically or differently by radicals selected from the group consisting of ($C_1$–$C_4$)-alkyl, ($C_1$–$C_4$)-alkoxy and —SO$_2$NR$^{10}$R$^{11}$, in which R$^{10}$ and R$^{11}$ independently of one another are hydrogen or ($C_1$–$C_4$)-alkyl,
R$^2$ and R$^3$ denote hydrogen,
R$^4$ denotes methyl or ethyl,
R$^5$ denotes methyl,
R$^6$ denotes hydrogen or methyl,
L denotes carbonyl or hydroxymethanediyl, and
R$^7$ denotes n-butyl, n-pentyl, n-hexyl or n-pent-4-en-1-yl.

5. Process for the preparation of a compound of the general formula (I) according to claim 1,
where
[A] a compound of the general formula (IIa),

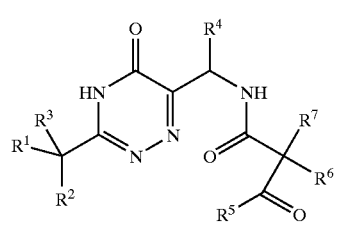

(IIa)

in which $R^1$, $R^2$, $R^3$, $R^4$, $R^5$, $R^6$ and $R^7$ have the meaning indicated in claim 1, is reacted under suitable condensation conditions to give a compound of the general formula (Ia)

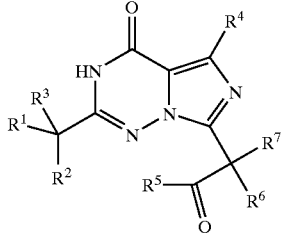

(Ia)

in which $R^1$, $R^2$, $R^3$, $R^4$, $R^5$, $R^6$ and $R^7$ have the meaning indicated in claim 1, and then, if appropriate,

[B] is reduced under suitable conditions to give a compound of the general formula (Ib)

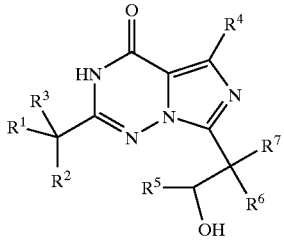

(Ib)

in which $R^1$, $R^2$, $R^3$, $R^4$, $R^5$, $R^6$ and $R^7$ have the meaning indicated in claim 1.

6. A compound of the general formula (II),

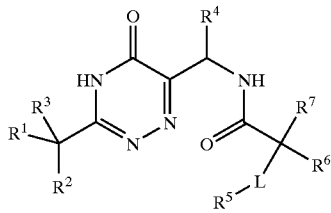

(II)

in which $R^1$, $R^2$, $R^3$, $R^4$, $R^5$, $R^6$, $R^7$ and L have the meaning indicated in claim 1.

7. A pharmaceutical composition comprising a compound according to claim 1 in combination with pharmaceutically acceptable excipients.

8. A method for improving perception, concentration power, learning power and/or memory power comprising administering to a subject an effective amount of a compound according to claim 1.

9. A method for the treatment of disorders of perception, concentration power, learning power and/or memory power comprising administering to a subject an effective amount of a compound according to claim 1.

10. The method according to claim 9, wherein the disorder is a result of dementia.

11. A method for the treatment of dementia comprising administering to a subject an effective amount of a compound according to claim 1.

* * * * *